US009018012B2

(12) United States Patent
Williams

(10) Patent No.: US 9,018,012 B2
(45) Date of Patent: Apr. 28, 2015

(54) VECTORS AND METHODS FOR GENETIC IMMUNIZATION

(75) Inventor: James A. Williams, Lincoln, NE (US)

(73) Assignee: Nature Technology Corporation, Lincoln, NE (US)

( * ) Notice: Subject to any disclaimer, the term of this patent is extended or adjusted under 35 U.S.C. 154(b) by 1808 days.

(21) Appl. No.: 11/814,311

(22) PCT Filed: Jan. 20, 2006

(86) PCT No.: PCT/US2006/002174
§ 371 (c)(1),
(2), (4) Date: Jul. 19, 2007

(87) PCT Pub. No.: WO2006/078979
PCT Pub. Date: Jul. 27, 2006

(65) Prior Publication Data
US 2008/0145376 A1    Jun. 19, 2008

Related U.S. Application Data

(60) Provisional application No. 60/645,078, filed on Jan. 20, 2005.

(51) Int. Cl.
*C12N 15/87* (2006.01)
*A61K 39/00* (2006.01)
*C12N 15/85* (2006.01)

(52) U.S. Cl.
CPC .............. *A61K 39/00* (2013.01); *A61K 2039/53* (2013.01); *C12N 15/85* (2013.01); *C12N 2800/106* (2013.01); *C12N 2800/107* (2013.01); *C12N 2830/15* (2013.01)

(58) Field of Classification Search
USPC .......................................................... 435/466
See application file for complete search history.

(56) References Cited

U.S. PATENT DOCUMENTS

| 6,103,470 | A | 8/2000 | Eastman et al. |
|---|---|---|---|
| 6,248,565 | B1 | 6/2001 | Williams |
| 6,410,220 | B1 | 6/2002 | Hodgson et al. |
| 6,500,432 | B1 | 12/2002 | Dalemans |
| 2003/0104444 | A1 | 6/2003 | Crouzet et al. |
| 2003/0143204 | A1 | 7/2003 | Lewis et al. |
| 2003/0180949 | A1 | 9/2003 | Levy |
| 2004/0009469 | A1 | 1/2004 | Apt et al. |
| 2004/0096462 | A1 | 5/2004 | Rangarajan |
| 2004/0110295 | A1 | 6/2004 | Punnonen et al. |
| 2004/0121348 | A1 | 6/2004 | Kreutzer et al. |
| 2004/0126845 | A1 | 7/2004 | Eenennaam et al. |
| 2004/0234543 | A1 | 11/2004 | Carrera |
| 2004/0235121 | A1 | 11/2004 | Smider |
| 2004/0241140 | A1 | 12/2004 | Pavlakis |
| 2004/0241177 | A1 | 12/2004 | Frazer |
| 2004/0242521 | A1 | 12/2004 | Gorenstein et al. |
| 2004/0253232 | A1 | 12/2004 | Jakobovits et al. |

OTHER PUBLICATIONS

Adams et al, Complete Nucleotide Sequence of a Mouse VL30 Retro-Element, Aug. 1988, Molecular and Cellular Biology, vol. 8, No. 8, pp. 2989-2998.
Applequist et al, Activation of Innate Immunity, Inflammation and Potentiation of DNA Vaccination Through Mammalian Expression of the TLR5 Agonist Flagellin, 2005, The Journal of Immunology, vol. 175, pp. 3882-3891.
Arruda et al, DNA Vaccine Encoding Human Immunodeficiency Virus-1 Gag, Targeted to the Major Histocompatibility Complex II Compartment by Lysosomal-Associated Membrane Protein, Elicits Enhanced Long-Term Memory Response, 2004, Immunology, vol. 112, pp. 126-133.
Aslanidis et al, Minimal Length Requirement of the Single-Stranded Tails for Ligation-Independent Cloning (LIC) of PCR Products, 1994, PCR Methods and Applications, vol. 4, pp. 172-177.
Barchet et al, Dendrtic Cells Respond to Influenza Virus Through TLR7- and PKR- Independent Pathways, 2005, European Journal of Immunology, vol. 35, pp. 236-242.
Barouch et al, A Human T-Cell Leukemia Virus Type 1 Regulatory Elemet Enhances the Immunogenicity of Human Immunodeficiency Virus Type 1 DNA Vaccines in Mice and Nonhuman Primates, Jul. 2005, Journal of Virology, vol. 79, No. 14, pp. 8828-8834.
Barry et al, Protection Against *Mycoplasma* Infection Using Expression-Library Immunization, Oct. 19, 1995, Letters to Nature, vol. 377, pp. 632-635.
Berglund et al, Enhancing Immune Responses Using Suicidal DNA Vaccines, Jun. 1998, Nature Biotechnologies, vol. 16, pp. 562-565.
Bichara et al, Genetic Instability Within Monotonous Runs of CpG Sequences in *Escherichia coli*, Jul. 1995, Genetics, vol. 140, pp. 897-907.
Bowen et al, Apoptosis Regulators and Responses in Human Melanocytic and Keratinocytic Cells, Jan. 2003, The Journal of Investigative Dermatology, vol. 120, No. 1, pp. 48-55.
Buchan et al, Electroporation as a "Prime/Boost" Strategy for Naked DNA Vaccination Against a Tumor Antigen, 2005, The Journal of Immunology, vol. 174, pp. 6292-6298.
Bucht et al, Modifying the Cellular Transport of DNA-Based Vaccines Alters the Immune Response to Hantavirus Nucleocapsid Protein, 2001, Vaccine, vol. 19, pp. 3820-3829.
Burgess et al, Human Skeletal Muscle Cytosols are Refractory to Cytochrome C-Dependent Activation of Type-II Caspases and Lack APAF-1, 1999, Cell Death Differentiation, vol. 6, pp. 256-261.
Capecchi et al, The Genome Revolution in Vaccine Research, 2004, Current Issues in Molecular Biology, vol. 6, pp. 17-28.

(Continued)

*Primary Examiner* — J. E. Angell
(74) *Attorney, Agent, or Firm* — Brooks Kushman P.C.

(57) ABSTRACT

Improved DNA vaccine plasmids are disclosed. The improved plasmids eliminate all extraneous sequences, and have superior eukaryotic expression, improved yield and stability during bacterial production, facilitate flexible targeting of antigens to various intracellular destinations, and novel RNA-based functionality. These vectors are utilized in novel immunization methods wherein combinations of immunostimulatory DNA vaccine plasmids that target antigens to various intracellular destinations are used to elicit improved immune response.

8 Claims, 13 Drawing Sheets

(56) References Cited

OTHER PUBLICATIONS

Figure 1:
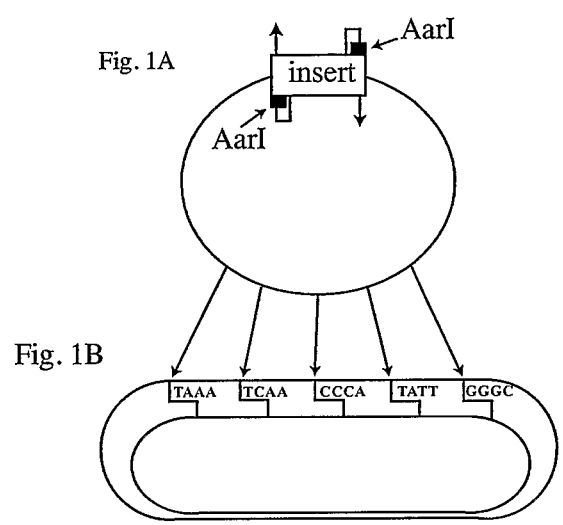

Chattergoon et al, Co-Immunization With Plasmid IL-12 Generates a Strong T-Cell Memory Response in Mice, 2004, Vaccine, vol. 22, pp. 1744-1750.
Chen et al, Universal Restriction Site-Free Cloning Method Using Chimeric Primers, Mar. 2002, BioTechniques, vol. 32, No. 3, pp. 518-520.
Coljee et al, Seamless Gene Engineering Using RNA- and DNA-Overhang Cloning, Jul. 2000, Nature Biotechnology (Technical Reports), vol. 18, pp. 789-791.
Crozat et al, TLR7: A New Sensor of Viral Infection, May 4, 2004, PNAS, vol. 101, No. 18, pp. 6835-6836.
Dean et al, Sequence Requirements for Plasmid Nuclear Import, 1999, Experimental Cell Research, vol. 253, pp. 713-722.
Delogu et al, DNA Vaccination Against Tuberculosis: Expression of a Ubiquitin-Conjugated Tuberculosis Protein Enhances Antimycobacterial Immunity, Jun. 2000, Infection and Immunity, nol 68, No. 6, pp. 3097-3102.
Diebold et al, Innate Antiviral Responses by Means of TLR7-Mediated Recognition of Single-Stranded RNA, Mar. 5, 2004, Science, vol. 303, pp. 1529-1531.
Viret et al, Meganuclease I-Scel as a Tool for the Easy Subcloning of Large DNA Fragments Devoid of Selection Marker, 1993, Biotechniques, vol. 14, No. 3, pp. 324-325.
Fitzwater et al, Conditional High Copy No. ColE1 Mutants: Resistance to RNA 1 Inhibition in vivo and in vitrol, 1988, The EMBO Journal, vol. 7, No. 10, pp. 3289-3297.
Flo, Co-Immunization with Plasmids Coding the Full Length and a Soluble Form of Glycoprotein D of HSV-2 Induces Protective Cellular and Humoral Immune Response in Mice, 2003, Vaccine, vol. 21, pp. 1239-1245.
Garg et al, The Hybrid Cytomegalovirus Enhancer/Chicken 'Beta'-Actin Promoter Along with Woodchuck Hepatitus Virus Posttranscriptional Regulatory Element Enhances the Protective Efficacy of DNA Vaccines, 2002, The Journal of Immunology, vol. 173, pp. 550-558.
Gerber et al, Phosphatidylinositol Glycan (PI-G) Anchored Membrane Proteins: Amino Acid Requirements Adjacent to the Site of Cleavage and PI-G Attachment in the COOH-Terminal Signal Peptide, Jun. 15, 1992, The Journal of Biological Chemistryvol 267, No. 17, pp. 12168-12173.
Ghersa et al, Commonly Used cat Reporter Vectors Contain a cAMP-Inducible, Cryptic Enhancer that Co-Operates with NF-_B-Sites, 1994, Gene, vol. 151, pp. 331-332.
Giantonio et al, Toxicity and Response Evaluation of the Interferon Inducer poly ICLC Administered at Low Dosein Advanced Renal Carcinoma and Relaped or Refractory Lymphoma: A Report of Two Clinical Trials of the Eastern Cooperative Oncology Group, 2001, Investigational New Drugs, vol. 19, pp. 89-92.
Graessmann et al, Helper Activity for Gene Expression, A Novel Function of the SV40 Enhancer, 1989, Nucleic Acids Research, vol. 17, No. 16, pp. 6603-6612.
Gurunathan et al, DNA Vaccines: Immunology, Application and Optimization, 2000, Annu Rev Immunol, vol. 18, pp. 927-974.
Hartikka et al, An Improved Plasmid DNA Expression Vector for Direct Injection into Skeletal Muscle, Jun. 20, 1996, Human Gene Therapy, vol. 7, pp. 1205-1217.
Heil et al, Species-Specific Recognition of Single-Stranded RNA via Toll-Like Receptor 7 and 8, Mar. 5, 2004, Science, vol. 303, pp. 1526-1529.
Hornung et al, Sequence-Specific Potent Induction of IFN-'Alpha' by Short Interfering RNA in Plasmacytoid Dendritic Cells Through TLR7, Mar. 2005, Nature Medicine, vol. 11, No. 3, pp. 263-270.
Imoto et al, Needle-Free Jet Injection of a Mixture of Japanese Encephalitis DNA and Protein Vaccine: A Strategy to Effectively Enhance Immunogenicity of the DNA Vaccine in a Murine Model. 2005, Viral Immunology, vol. 18, No. 1, pp. 205-212.
Kalai et al, Tipping the Balance Between Necrosis and Apoptosis in Human and Murine Cells Treated With Interferon and dsRNA, 2002, Cell Death and Differentiation, vol. 9, pp. 981-994.
Kato, Polypyrimidine/Polypurine Sequence in Plasmid DNA Enhances Formation of Dimer Molecules in *Escherichia coli*, 1993, Molecular Biology Reports, vol. 18, pp. 183-187.
Kim et al, Enhancement of Suicidal DNA Vaccine Potency by Delaying Suicidal DNA-Induced Cell Death, 2004, Gene Therapy, vol. 11, pp. 336-342.
Kushner et al, Eukaryotic Regulatory Elements Lurking in Plasmid DNA: The Activator Protein-1 Site in pUC, 1994, Molecular Endocrinology, vol. 8, No. 4, pp. 405-407.
Kutzler et al, Coimmunization with an Optimized IL-15 Plasmid Results in Enhanced Function and Longevity of CD8 T Cells that are Partially Independent of CD4 T Cell Help, 2005, The Journal of Immunology, vol. 175, pp. 112-123.
Lebedenko et al, Method of Artificial DNA Splicing by Directed Ligation (SDL), 1991, Nucleic Acids Research, vol. 19, No. 24, pp. 6757-6761.
Lee et al, Immuno-Stimulatory Effects of Bacterial-Derived Plasmids Depend on the Nature of the Antigen in Intramuscular DNA Inoculations, 1998, Immunology, vol. 94, pp. 285-289.
Leifert et al, Targeting Plasmid-Encoded Proteins to the Antigen Presentation Pathway, 2004, Immunological Reviews, vol. 199, pp. 40-53.
Leite et al, Negative Effect of a cis-acting pBR322 Element on Adenovirus Ela Gene Expression, 1989, Gene, vol. 82, pp. 351-356.
Leitner et al, Enhancement of Tumor-Specific Immune Response with Plasmid DNA Replicon Vectors, Jan. 1, 2000, Cancer Research, vol. 60, pp. 51-55.
Leitner et al, Alphavirus-Based DNA Vaccine Breaks Immunological Tolerance by Activating Innate Antiviral Pathways, Jan. 2003, Nature Medicine, vol. 9, No. 1, pp. 33-39.
Leitner et al, DNA Vaccines and Apoptosis: To Kill or Not to Kill?, Jul. 2003, The Journal of Clinical Investigation, vol. 112, No. 1, pp. 22-24.
Leitner et al, Apoptosis is Essential for the Increased Efficacy of Alphaviral Replicase-Based DNA Vaccines, 2004, Vaccine, vol. 22, pp. 1537-1544.
Lemieux, Technological Advances to Increase Immunogenicity of DNA Vaccines, 2002, Expert Rev Vaccines, vol. 1, No. 1, pp. 85-93.
Liew et al, Negative Regulation of Toll-Like Receptor-Mediated Immune Responses, Jun. 2005, Nature Reviews: Immunology, vol. 5, pp. 446-458.
Lin-Chao et al, High Copy Number of the pUC Plasmid Results From a Rom/Rop-Suppressible Point Mutation in RNA II, 1992, Molecular Microbiology, vol. 6, No. 22, pp. 3385-3393.
Liu et al, Polynucleotide Viral Vaccines: Codon Optimization and Ubiquitin Conjugation Enhances Prophylactic and Therapeutic Efficacy, 2002, Vaccine, vol. 20, pp. 862-869.
Manoj et al, Approaches to Enhance the Efficacy of DNA Vaccines, 2004, Critical Reviews in Clinical Laboratory Sciences, vol. 41, No. 1, pp. 1-39.
Marques et al, Activation of the Mammalian Immune System by siRNAs, Nov. 2005, Nature Biotechnology: Review, vol. 23, No. 11, pp. 1399-1405.
Marques et al, HIV-1 p55Gag Encoded in the Lysosome-Associated Membrane Protein-1 as a DNA Plasmid Vaccine Chimera Is Highly Expressed, Traffics to the Major Histocompatibility Class II Compartment, and Elicits Enhanced Immune Responses, Sep. 26, 2003, The Journal of Biological Chemistry, vol. 278, No. 39, pp. 37926-37936.
Matsumoto et al, Toll-Like Receptor 3: A Link Between Toll-Like Receptor, Interferon and Viruses, 2004, Microbiol Immunol, vol. 48, No. 3, pp. 147-154.
Matsumoto et al, Analysis of Double-Stranded RNA-Induced Apoptosis Pathways Using Interferon-Response Noninducible Small Interfering RNA Expression Vector Library, Jul. 8, 2005, The Journal of Biological Chemistry, vol. 280, No. 27, pp. 25687-25696.
Mesika et al, A Regulated, NF_B-Assisted Import of Plasmid DNA into Mammalian Cell Nuclei, May 2001, Molecular Therapy, vol. 3, No. 5, pp. 653-657.

(56) References Cited

OTHER PUBLICATIONS

Mestas et al, Of Mice and Not Men: Differences Between Mouse and Human Immunology, 2004, The Journal of Immunology, vol. 172, pp. 2731-2738.
Mukhopadhyay et al, The Potential for Toll-Like Receptors to Collaborate With Other Innate Immune Receptors, 2004, Immunology, vol. 112, pp. 521-530.
Nam et al, Inhibition of Both Extrinsic and Intrinsic Death Pathways Through Nonhomotypic Death-Fold Interactions, Sep. 24, 2004, Molecular Cell, vol. 15, pp. 901-912.
Napolitani et al, Selected Toll-Like Receptor Agonist Combinations Synergistically Trigger a T Helper Type 1-Polarizing Program in Dendritic Cells, Aug. 2005, Nature Immunology: Articles, vol. 6, No. 8, pp. 769-776.
Pebernard et al, Determinants of Interferon-Stimulated Gene Induction by RNAi Vectors, 2004, Differentiation, vol. 72, pp. 103-111.
Peterson et al, Context-Dependent Gene Expression: cis-Acting Negative Effects of Specific Procaryotic Plasmid Sequences on Eucaryotic Genes, Apr. 1987, Molecular and Cellular Biology, vol. 7, No. 4, pp. 1563-1567.
Piechocki et al, Complementary Antitumor Immunity Induced by Plasmid DNA Encoding Secreted and Cytoplasmic Human ErbB-2, 2001, The Journal of Immunology, pp. 3367-3374.
Primeau et al, Apoptosis in Heart and Skeletal Muscle, 2002, Can J Appl Physiol, vol. 27, No. 4, pp. 349-395.
Ramanathan et al, Choice of Expression Vector Alters the Localization of a Human Cellular Protein, 2001, DNA and Cell Biology, vol. 20, No. 2, pp. 101-105.
Rosati et al, DNA Vaccines Expressing Different Forms of Simian Immunodeficiency Virus Antigens Decrease Viremia Upon SIVmac251 Challenge, Jul. 2005, Journal of Virology, vol. 79, No. 13, pp. 8480-8492.
Sasaki et al, Apoptosis-Mediated Enhancement of DNA-Raised Immune Responses by Mutant Caspases, Jun. 2001, Nature Biotechnology, vol. 19, pp. 543-547.
Satoh et al, Autoantibodies Define a Family of Proteins With Conserved Double-Stranded RNA-Binding Domains as Well as DNA Binding Activity, Dec. 3, 1999, The Journal of Biological Chemistry, vol. 274, No. 49, pp. 34598-34604.
Schroder et al, TLR3 in Antiviral Immunity: Key Player or Bystander?, Sep. 2005, TRENDS in Immunology, vol. 26, No. 9, pp. 462-468.
Smith et al, Generation of Cohesive Ends on PCR Products by UDG-Mediated Excision of dU and Application for Cloning into Restriction Digest-Linearized Vectors, 1993, PCR Methods and Applications, vol. 2, pp. 328-332.
Sugiyama et al, CpG RNA: Identification of Novel Single-Stranded RNA That Stimulates Human CD14 CD11c Monocytes, 2005, The Journal of Immunology, pp. 2273-2279.
Suzuki et al, Activation of Target-Tissue Immune-Recognition Molecules by Double-Stranded Polynucleotides, Mar. 1999, Proc Natl Acad Sci USA, vol. 96, pp. 2285-2290.
Sykes et al, Linear Expression Elements: A Rapid, in Vivo, Method to Screen for Gene Functions, Apr. 1999, Nature Biotechnology, vol. 17, pp. 355-359.
Toka et al, Molecular Adjuvants for Mucosal Immunity, 2004, Immunological Reviews, vol. 199, pp. 100-112.
Tully et al, pBR322 Contains Glucocorticoid Regulatory Element DNA Consensus Sequences, Apr. 14, 1987, Biochemical and Biophysical Research Communication, vol. 144, No. 1, pp. 1-10.
Wang et al, Noncoding RNA Danger Motifs Bridge Innate and Adaptive Immunity and are Potent Adjuvants for Vaccination, Oct. 2002, The Journal of Clinical Investigation, vol. 110, No. 8, pp. 1175-1184.
Wang et al, Effects of Length and Location on the Cellular Response to Double-Stranded RNA, Sep. 2004, Microbiology and Molecular Biology Reviews, vol. 68, No. 3, pp. 432-452.
Whitmore et al, Synergistic Activation of Innate Immunity by Double-Stranded RNA and CpG DNA Promotes Enhanced Antitumor Activity, Aug. 14-15, 2004, Cancer Research, vol. 64, pp. 5850-5860.
Wizemann et al, Use of a Whole Genome Approach to Identify Vaccine Molecules Affording Protection Against *Streptococcus pneumoniae* Infection, Mar. 2001, Infection and Immunity, vol. 69, No. 3, pp. 1593-1598.
Wu et al, Engineering an Intracellular Pathway for Major Histocompatibility Complex Class II Presentation of Antigens, Dec. 1995, Proc Natl Acad Sci USA, vol. 92, pp. 11671-11675.
Xu et al, Endoplasmic Reticulum Targeting Sequence Enhances HBV-Specific Cytotoxic T Lymphocytes Induced by a CTL Epitope-Based DNA Vaccine, 2005, Virology, vol. 334, pp. 255-263.
Zaman et al, Plasmid Recombination by the RecBCD Pathway of *Escherichia coli*, Jul. 1996, Journal of Bacteriology, vol. 178, No. 13, pp. 3840-3845.
Zare et al, Arthritogenic Properties of Double-Stranded (Viral) RNA, 2004, The Journal of Immunology, vol. 172, pp. 5656-5663.
Zheng et al, Activation of the Protein Kinase PKR by Short Double-Stranded RNAs with Single-Stranded Tails, 2004, RNA, vol. 10, pp. 1934-1945.
Zinckgraf et al, Modulating Gene Expression Using DNA Vaccines With Different 3'-UTRs Influences Antibody Titer, Seroconversion and Cytokine Profiles, 2003, Vaccine, vol. 21, pp. 1640-1649.
Zhongming et al, Immunogenicity of DNA Vaccines Expressing Tuberculosis Proteins Fused to Tissue Plasminogen Activator Signal Sequences, Sep. 1999, Infection and Immunity, vol. 67, No. 9, pp. 4780-4786.
Zohar et al, Analysis of Genetic Control Elements in Eukaryotes: Transcriptional Activity or Nuclear Hitchhiking?, 2001, BioEssays, vol. 23, No. 12, pp. 1176-1179.
Operschall et al, Mechanism of Protection Against Influenza A Virus by DNA Vaccine Encoding the Hemagglutinin Gene, 2000, Intervirology, vol. 43, pp. 322-330.
Liu et al, Polynucleotide Viral Vaccines: Codon Optimization and Ubiquitin Conjugation Enhances Prophylactic and Therapeutic Efficacy, Dec. 2001, Vaccine, vol. 20, Issues 5-6, pp. 862-869.
Bode et al, The Transgeneticist's Toolbox: Novel Methods for the Targeted Modification of Eukaryotic Genomes, Biol. Chem., 2000, vol. 381, pp. 801-813.
Thomson et al, "Delivery of Multiple CD8 Cytotoxic T Cell Epitopes by DNA Vaccination," J. Immunol. 1998, v. 160 (4), pp. 1717-1723.
Williams et al., "pDNAVACCultra vector family: high throughput intracellular targeting DNA vaccine plasmids," Vaccine, 2006, v. 24, pp. 4671-4676.
NTC Key 2006 Publications, Retrieved from the Internet <URL: http://epscor.unl.edu/pdfs/Clague%20Hodgson.pdf, 18 pages.
International Search Report mailed Oct. 27, 2008 for PCT/US06/02174, filed Jan. 20, 2006, 3 pgs.
International Search Report (revised version) mailed Jul. 15, 2009 for PCT/US06/02174, filed Jan. 20, 2006, 4 pgs.

Figure 2:
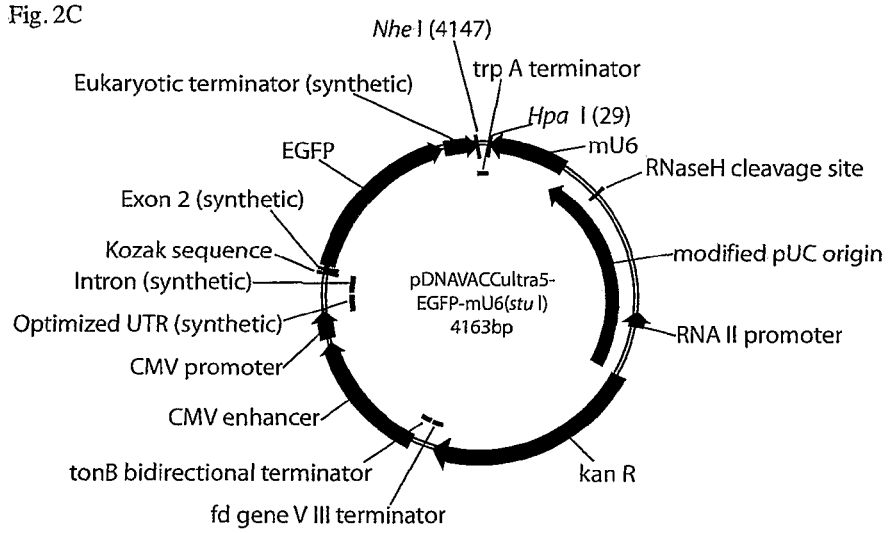
Figure 2:
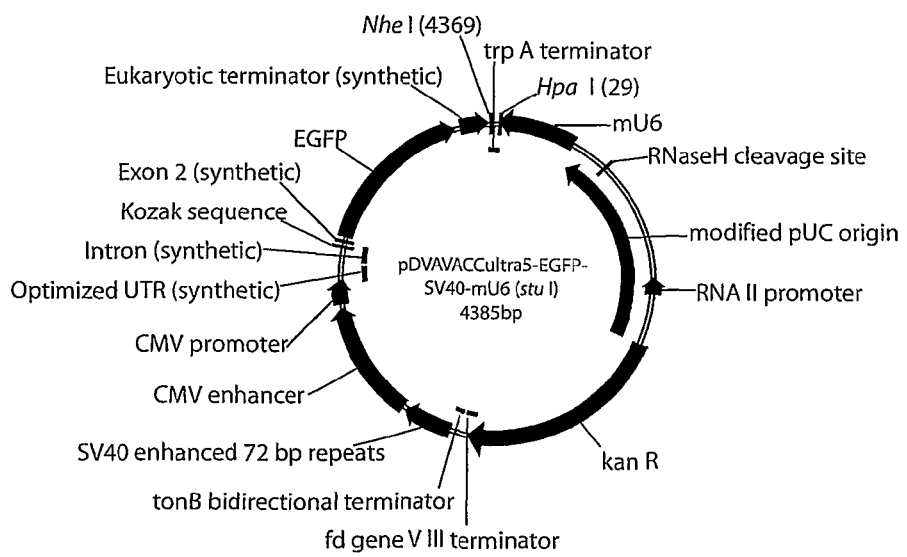

Figure 2
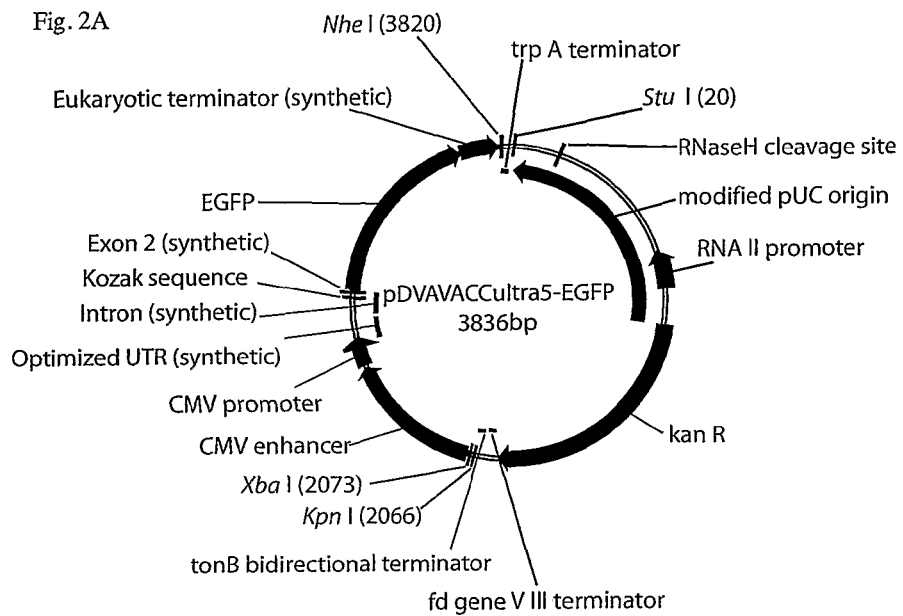
Fig. 2A
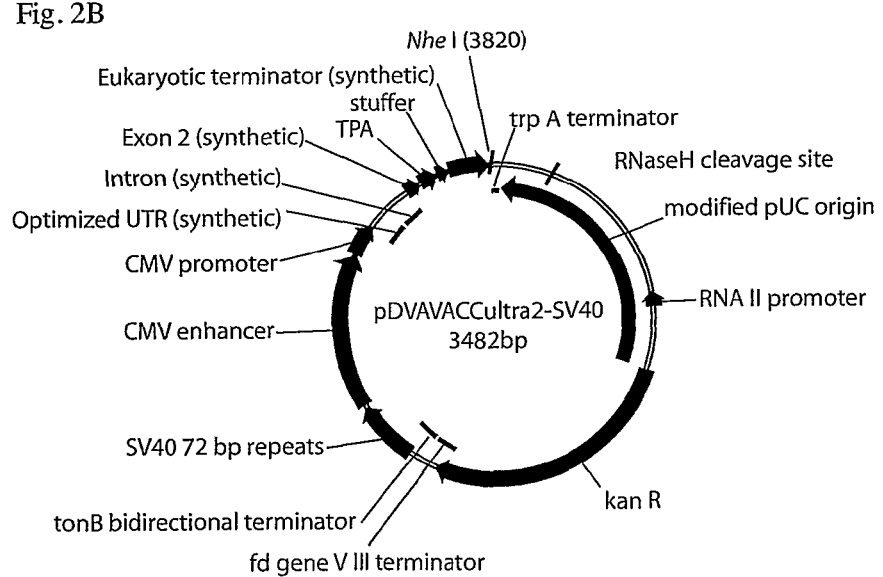
Fig. 2B

Figure 3
Fig 3A
Class IIS enzyme sites
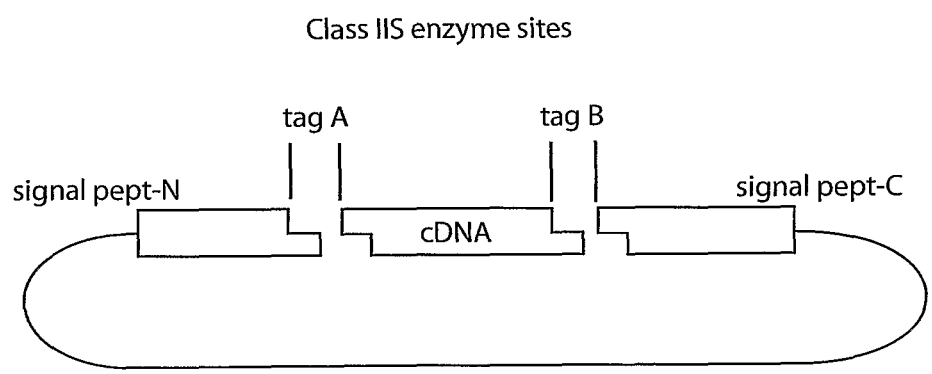
Fig 3B
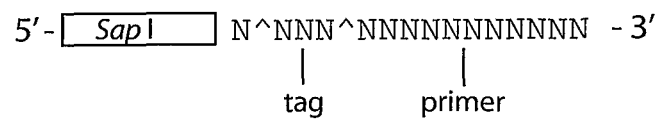

Figure 5G:
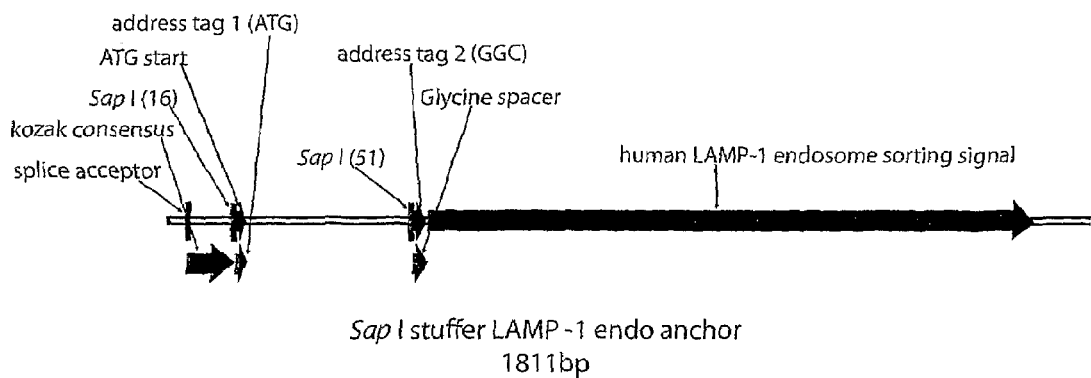
Figure 5H:
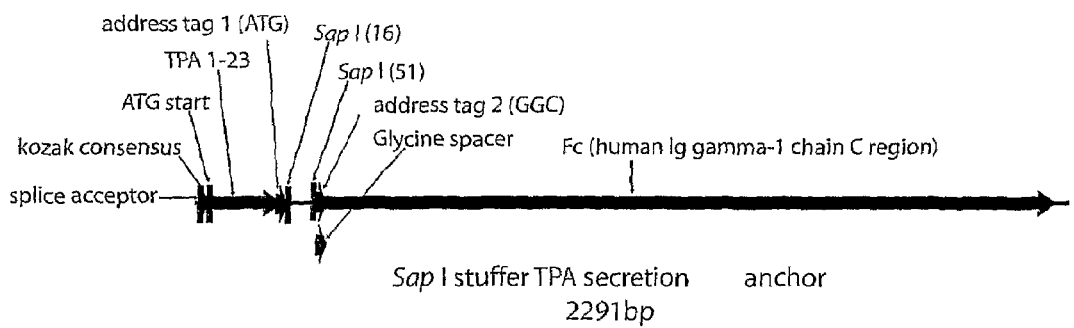

Figure 5
Fig 5A
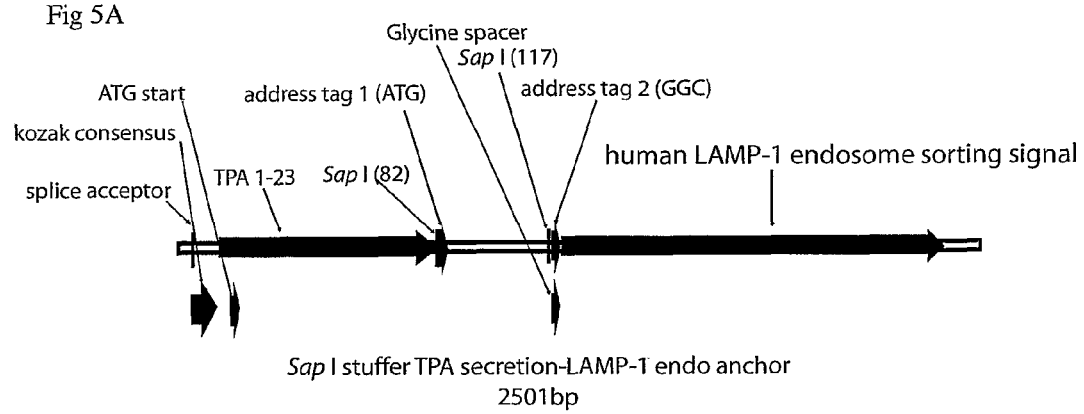
Sap I stuffer TPA secretion-LAMP-1 endo anchor
2501bp
Fig 5B
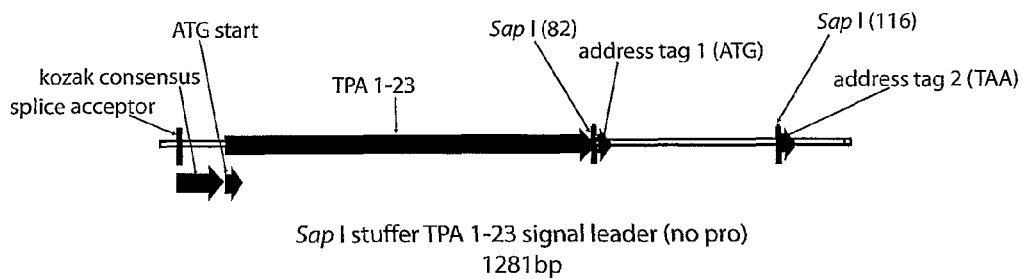
Sap I stuffer TPA 1-23 signal leader (no pro)
1281bp
Fig 5C
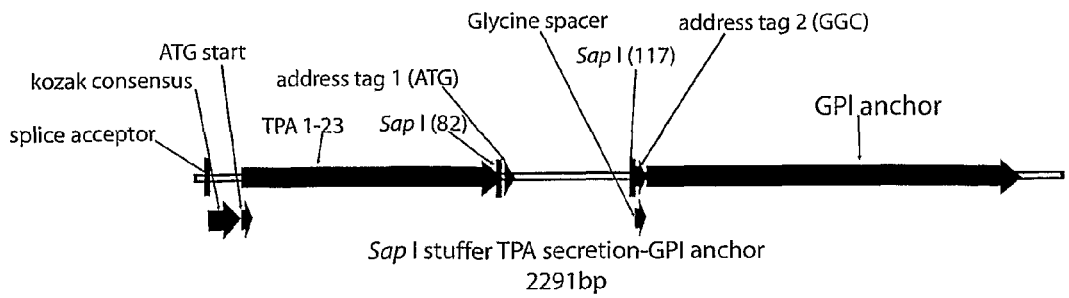
Sap I stuffer TPA secretion-GPI anchor
2291bp Fig 5D
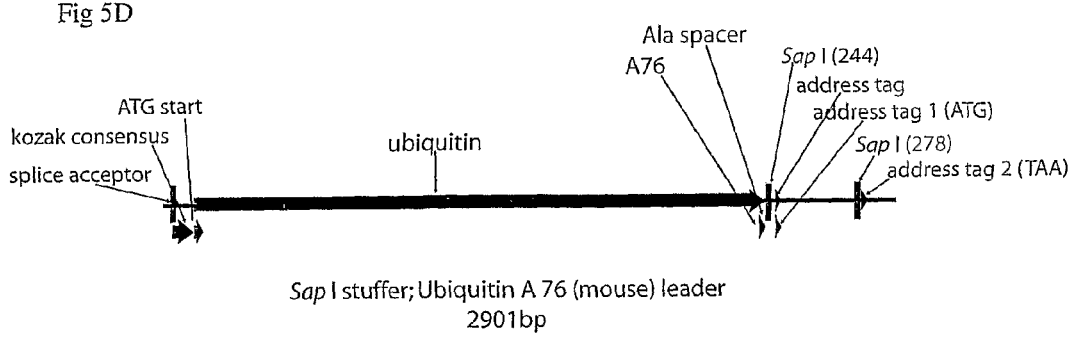
Sap I stuffer; Ubiquitin A 76 (mouse) leader
2901bp
Fig 5E
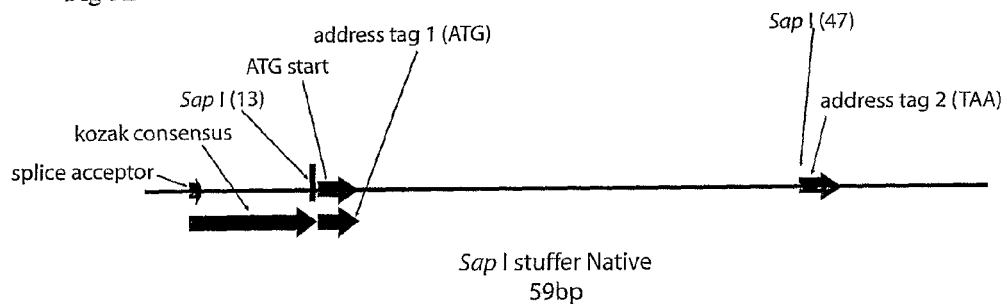
Sap I stuffer Native
59bp
Figure 5
Fig 5F
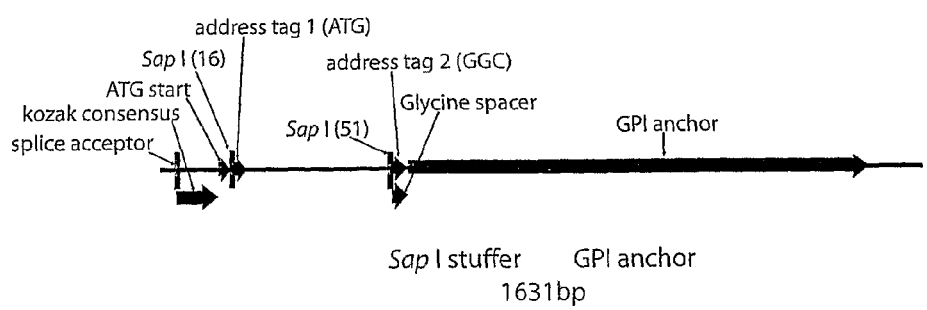
Sap I stuffer    GPI anchor
1631bp Sap I stuffer LAMP-1 endo anchor
1811bp Sap I stuffer TPA secretion    anchor
2291bp

VECTORS AND METHODS FOR GENETIC IMMUNIZATION

This application claims the benefit of Provisional Patent Application Ser. No. 60/645,078 filed 20 Jan. 2005.

STATEMENT REGARDING FEDERALLY SPONSORED RESEARCH OR DEVELOPMENT

Not applicable

FIELD OF THE INVENTION

The present invention relates to a family of eukaryotic expression plasmids, and immunization strategies, useful for obtaining improved genetic immunization, and more particularly, for customizing and improving the immune response to plasmid encoded antigens.

BACKGROUND OF THE INVENTION

The present invention is a family of eukaryotic expression plasmids, and immunization strategies, useful for genetic immunization. Such molecules and methods for use are useful in biotechnology, gene therapy, cancer and agriculture.

With the invention in mind, a search of the prior art was conducted. DNA vaccines (genetic vaccines) are a potential disruptive technology, that offer the promise of a new way to immunize humans (or animals) with materials that are entirely gene-based and expressed by the organism's own cells, making an ideal mimic of intracellular antigens.

Methods to improve immune responses to DNA vaccine plasmids are described in the art. For example, the efficacy of a DNA vaccine can be further improved, or tailored for systemic or mucosal immunity, or cancer, allergy, bacterial, intracellular parasite or viral targets, by; communization with costimulatory plasmids (e.g. IL12) to modulate the type of response ($T_H1$ versus $T_H2$ bias); cell death inhibitors or enhancers; or optimization of delivery (e.g. electroporation versus gene gun). Some such methods and molecules are described in Lemieux, P. 2002 *Expert Rev. Vaccines* 1: 85-93, Toka F N, Pack C D, Rouse B T. 2004 *Immunological reviews* 199: 100-112, and Gurunathan S, Klinman D M, Seder R A. 2000 *Annu. Rev. Immunol.* 18: 927-974 and are included herein by reference. DNA vaccination could also involve utilizing different delivery systems in the prime and the boost, as taught by Buchan S, Gronevik E. Mathiesen I, King C, Stevenson F K, Rice J. 2005 *Immunol.* 174: 6292-6298 or different injection sites, as taught by Pavlakis G N, Gragerov A, Felber B K. 2004 US Patent Application 2004/0241140.

DNA vaccination would significantly enhance the rapid deployment utility of DNA vaccines since development times for DNA vaccines are significantly shorter than those for protein or viral vector systems.

Current Obstacles

Protective immunity in humans and other primates has not been broadly obtained using DNA only vaccination. Primate efficacy has been obtained utilizing DNA vaccines in combination with a heterologous protein, inactivated organism, or viral vector boosting. Enhanced immune responses have also been reported when plasmid DNA and purified protein (corresponding to the protein encoded in the plasmid) (Dalemans W., Van Mechelen M V, Bruck C, Friede M. 2003 U.S. Pat. No. 6,500,432; Carrera S D, Grillo J M, de Leon LALP, Lasa A M, Feyt R P, Rodriguez A V, Obregon J C A, Rivero N A, Donato GM 200420040234543; and Imoto J, Konishi E. 2005 *Viral Immunol.* 18: 205-212) or inactivated virus (Rangarajan P N, Srinivasan V A, Biswas L, Reddy G S. 2004 US Patent Application 2004/0096462) are mixed and coinjected.

However, using plasmids in combination with inactivated organisms, proteins or viral vectors in a vaccine (either as a mixture, or sequentially in a prime boost) eliminates most of the benefits of DNA vaccination, including improved safety, reduced cost, and rapid deployment.

DNA vaccines may be incrementally improved by the following methodologies:

Antigen expression: The art teaches that one of the limitations of DNA vaccination is that antigen expression is generally very low. Vector modifications that improve antigen expression (e.g. codon optimization of the gene, inclusion of an intron, use of the strong constitutive CMV or CAGG promoters versus weaker or cell line specific promoter) are highly correlative with improved immune responses (reviewed in Manoj S, Babiuk L A, Drunen S V, en Hurk L V. 2004 *Critical Rev Clin Lab Sci* 41: 1-39). A hybrid CMV promoter (CMV/R) with 5- to 10-fold improved expression improved cellular immune responses to HIV DNA vaccines in mice and nonhuman primates (Barouch D H, Yang Z Y, Kong W P, Korioth-Schmitz B, Sumida S M, Truitt D M, Kishko M G, Arthur J C, Miura A, Mascola J R, Letvin N L, Nabel G J. 2005 *J Virol.* 79: 8828-8834). A plasmid containing the woodchuck hepatitis virus posttranscriptional regulatory element (a 600 bp element that increases stability and extranuclear transport of resulting in enhanced levels of mRNA for translation) enhanced antigen expression and protective immunity to HA in mice (Garg S, Oran A E, Hon H, Jacob J. 2002 *J Immunol.* 173: 550-558). These studies teach that improvement in expression beyond that of current CMV based vectors may generally improve immunogenicity in humans.

The art teaches that plasmid entry into the nucleus is a limiting factor in obtaining antigen expression. Increasing nuclear localization of a plasmid through inclusion of NFκB binding sites or a SV40 enhancer improves antigen expression in vitro and in vivo; this is presumed due to binding of NFκB which then piggybacks the plasmid to the nucleus (Dean D A, Dean B S, Muller S, Smith L C. 1999 *Experimental Cell Research* 253: 713-722). However, NFκB is generally cytoplasmically localized, and transfer to the nucleus is both limited, tissue-specific, and dependent on stimulatory signals. This limits the utility of NFκB nuclear targeting to improve DNA vaccination.

$T_H1$ or $T_H2$ bias: The art teaches that shifting immune response to DNA vaccine expressed viral or other antigens from $T_H2$ to $T_H1$ is desirable, to elevate humoral and cellular responses; for other applications, such as allergy, a $T_H2$ biased response is considered optimal. For example, CpG sequences (which promote $T_H1$ response) improved antibody and CTL responses to influenza hemaglutinin (HA), and CTL responses to influenza nucleoprotein DNA vaccines injected IM (Lee and Sung, 1998). Communization with IL12 or IL15 $T_H1$ adjuvants improves T cell responses to HA (Chattergoon M A, Saulino V, Shames J P, Stein J, Montaner L J, Weiner D B. 2004 *Vaccine* 22: 1744-1750; Kutzler M A, Robinson T M, Chattergoon M A, Choo D K, Choo A Y, Choe P Y, Ramamathan M P, Parkinson R, Kudchodkar S, Tamura Y, Sidhu M, Roopchand V, Kim J J, Pavlakis G N, Felber B K, Waldmann T A, Boyer J D, Weiner D B. 2005 *J Immunol* 175: 112-123) and antibody mediated protection (Operschall E, Pavlovic J, Nawrath M, Molling K. 2000 *Intervirol* 43: 322-330).

Immunostimulatory Adjuvants:

A number of microbial specific motifs have been identified that activate innate immunity through Toll like receptor (TLR) binding, for example, Tri-acyl lipopeptides (TLR-1/TLR2) peptidoglycan (TLR-2), dsRNA (TLR3), bacterial HSP60 or Lipopolysaccharide (LPS; TLR-4), flagellin (TLR5), Di-acyl lipopeptide (TLR-6) ssRNA (TLR-7, TLR-8) unmethylated CpG DNA (TLR-9). U-rich or U/G rich ssRNA TLR7/8 agonists have been identified that induce interferon responses (Heil F, Hemmi H, Hochrein H, Ampenberger F, Kirschning C, Akira S, Lipford G, Wagner H, Bauer S. 2004 *Science* 303: 1526-1529; Diebold S S, Kaisho T, Hemmi H, Akira S, e Sousa C R. 2004 *Science* 303: 1529-1531; Barchet W, Krug A, Cella M, Newby C, Fischer J A A, Dzionek A, Pekosz A, Colonna M. 2005 *Eur. J. Immunol*. 35: 236-242) as well as a sequence specific siRNA that induces interferon production from human and mice plasmacytoid dendritic cells through TLR-7 (Hornung V, Guenthner-Biller M, Bourquin C, Ablasser A, Schlee M, Uematsu S, Noronha A, Manoharan M, Akira S, de Fougerolles A, Endres S, Hartmann G. 2005 Nat. Med. 11: 263-270). A novel class of immunostimulatory nucleic acid, single stranded CpG RNA which does not require TLR-3, 7, 8 or 9 has also been identified (Sugiyama T, Gursel M, Takeshita F, Coban C, Conover J, Kaisho T, Akira S, Klimnan D M, Ishii K J. 2005 *J Immunol*. 174: 2273-2279).

These molecules can be utilized as adjuvants to improve DNA vaccination. However, exogenously applied adjuvant adds expense, complicates regulatory approval (an additional investigational entity in the vaccine) and requires high dosages since the adjuvant is not targeted (i.e. affects multiple cells in addition to cells containing the DNA vaccine); the high dose of untargeted adjuvant also presents special safety concerns (e.g. autoimmunity, sepsis)

Unmethylated CpG is present in the vector backbone of microbial produced plasmids and augmentation (CpG enriched plasmids) can be used to stimulate $T_H1$ responsive innate immune signals through TLR-9. Unfortunately, these effects are observed only with high dosages, and CpG effects are minimal with advanced delivery methods which use economically low amounts of antigen (e.g. gene gun) as reflected by a $T_H2$ biased response. As well, the overall poor immunological response to DNA vaccines in humans has been attributed, in part, to significantly reduced expression of TLR-9 in humans compared to mice.

Vector encoded protein TLR agonists potentially would induce the innate immune system at low dose, since the signal from these elements is "amplified" from the vector (rather than a fixed vector component such as CpG). Incorporation of a flagellin producing gene into the vector backbone activates innate immune responses and potentiated $T_H1$ bias and cellular immune response to an antigen delivered by Gene Gun. This demonstrates the potential for utilization of amplifiable TLR agonists to potentiate low dose DNA vaccination (Applequist S E, Rollman E, Wareing M D, Liden M, Rozell B, Hinkula J, Ljunggren H G. 2005 *J. Immunol.* 175: 3882-3891). However, for inclusion of an innate immunity inducer in a DNA vaccine vector backbone there should be no associated adaptive immune response since this would limit repeat usage and generate variable results in a population due to attenuated responses in individuals with prior exposure (preexisting immunity). Vectors such as alphaviral replicons (which produce dsRNA adjuvant) or the flagellin producing vector described above contain one or more proteins that can induce adaptive immunity to vector components and are unsuitable for repeat application.

In summary, the art does not teach how to obtain immunostimulatory effects of amplified TLR agonists without the requirement for heterologous proteins in the vector backbone, which leads to adaptive immune responses.

Cell death: The art teaches that cell death can augment immune responses to antigens. IM injection of influenza HA and NP DNA vaccines codelivered with mutant caspases that promote slow cell death enhanced T cell responses and cellular immunity (Sasaki S, Amara R R, Oran A E, Smith J M, Robinson H L. 2001 *Nat Biotechnol* 19: 543-547). The immune response to HA and NP is also dramatically enhanced (compared to DNA vaccines) utilizing Semliki forest alphavirus replicon (suicide) vaccines (Berglund P, Smerdou C, Fleeton M N, Tubulekas I, Liljestrom P. 1998 *Nature Biotech* 16: 562-565) that induce apoptosis; cell death is critical for the improved immune response. Replicon vectors contain multiple viral replication proteins; immune response against these proteins may limit repeat usage. Apoptotic cell death has also been accomplished by coadministering Fas or mutated caspases 2 or 3, which enhances CTL responses to IM administered DNA vaccines. Coadministered caspases also improves immune responses to influenza HA DNA vaccine by Gene Gun (Sasaki et al, Supra 2001). The optimal condition may be to selectively kill muscle or keratinocyte cells (but not immune cells) for a source of antigen for dendritic or langerhans cells (Reviewed in Leitner W W, Restifo N P. 2003 *J Clin invest* 112: 22-24). This is not possible utilizing constitutive cell death promoting agents. Inhibition of apoptosis can also improve immune responses, wherein coadministering antiapoptotic Bcl-XL strongly enhanced T cell response after Gene Gun administration. This may reflect a benefit of prolonging dendritic cell lifespan. However, the use of cell death inhibitors may predispose cells to transformation (in the case of integrated plasmids) and increase cancer risk.

Cytoplasmic dsRNA activates PKR and RIG-1, which induces interferon production, inhibits protein synthesis thus reducing antigen production eventually leading to apoptotic cell death (reviewed in Wang Q, Carmichael G G. 2004 *Microb. Molec. Biol. Rev.* 68: 432-452). Cell death releases the dsRNA, which can then be taken up by cells, and further induce innate immune response by binding and stimulating endosomally localized TLR-3 (Reviewed in Schroder M, Bowie AG. 2005 *Trends Immunol.* 26: 462-468). The art teaches that this type of dsRNA stimulation occurs with alphavirus replicon vaccines. Alphavirus replicon (suicide) vaccines induce enhanced immune responses with 100-1000 fold less antigen compared to standard DNA vaccines (by IM injection). These vectors induce apoptosis, presumed through formation of dsRNA which activates antiviral pathways and eventually leads to apoptotic cell death (Leitner W W, Ying H, Driver D A, Dubensky T W, Restifo N P. 2000 *Cancer Research* 60: 51-55). Cell death is required for improved vaccine efficacy and is mediated by cytoplasmic replicon dsRNA; it is possible that dsRNA in apoptotic elements are phagocytosed by APC's, and induce innate immunity through the endosomal TLR-3 dsRNA recognition pathway. Codelivery of anti-apoptotic gene (Bcl-XL) reduced protection, despite increasing antigen production (Leitner W W, Hwang L N, Bergmann-Leitner E S, Finkelstein S E, Frank S, Restifo N P. 2004 *Vaccine* 22: 1537-1544; Leitner W W, Hwang L N, DeVeer M J, Zhou A, Silverman R H, Williams B R G, Dubensky T W, Ying H, Restifo N P. 2003 *Nature Med* 9: 33-39; Matsumoto S, Miyagishi M, Akashi H, Nagai R, Taira K. 2005 *J Biol Chem* 280: 25687-25696). However, a delivery dependent balance between cell death signals and optimal production of antigen is required, since suicide DNA vaccines are not effective with Gene Gun delivery (which targets dendritic cells) unless an anti-apoptosis gene is included (Kim T W, Hung C F, Juang J, He L, Hardwick J M, Wu T C. 2004 *Gene Ther* 11: 336-342).

Antigen targeting: Poor immunogenicity has partially been solved by altering the intracellular localization using targeting fusion tags. It is established in the art that fusion proteins that alter the intracellular localization of an antigen (e.g. from cytoplasmic to secreted) or otherwise target antigen presenting pathways alter the resulting immune response (reviewed in Gurunathan et al, Supra 2000). Molecules that can be used to alter intracellular trafficking or antigen presentation of fused proteins are known in the art. Several intracellular targeting sequences are described in Williams W V, Madaio M, Weiner D B. 2001 U.S. Pat. No. 6,248,565 B1 and are included herein by reference. Several antigen presentation pathway targeting molecules are described in Leifert J A, Rodriguez-Carreno M P, Rodriguez F, Whitton J L 2004 *Immunological reviews* 199: 40-53 and Lemieux, Supra 2002 and are included herein by reference. Some of these are summarized in Table 3.

For example, it has been demonstrated that targeting heterologous proteins to various intracellular destinations including, but not limited to, secreted (e.g. TPA; Zhongming L, Howard A, Kelley C, Delogu G, Collins F, Morris S. 1999 *Infect Immun*. 67: 4780-4786), membrane-anchored (e.g. human alkaline phosphatase (PLAP; Gerber L, Kodukula K, Udenfriend S. 1992 *J Biol Chem* 267: 12168-12173), endosome (e.g. human LampI; Wu, T, Guarnieri F G, Staveley-O'Carroll K F, Viscidi R P, Levitsky H I, Hedrick L, Cho K R, August J T, Pardoll D M. 1995 *Proc. Natl. Acad. Sci.* 92: 11671-11675), proteosome (e.g. mouse Ubiquitin A76; Delogu G, Howard A, Collins F M, and Morris S L. 2000 *Infect. Immun.* 68: 3097-3102), or endoplasmic reticulum (Xu W, Chu Y, Zhang R, Xu H, Wang Y. Xiong S 2005 *Virology* 334: 255-263) alter or enhance immune responses. Endosomal targeting promotes a MHC class II response, while the destabilizing ubiquitin molecule (UbiquitinA76 versus native UbiquitinG76) is utilized to enhance entry into proteosomal degradation pathway and MHC class I presentation.

It is also well known in the art that the effects of intracellular targeting are antigen specific, and the optimal intracellular destination to create the desired immune response need to be determined empirically for each antigen.

Despite the improvements in immunogenicity obtained by fusion of an antigen to such targeting sequences, efficacy has not been obtained in humans or other primates using the modified antigens.

A further incremental improvement is to immunize with a mix of DNA Vaccine plasmids, each encoding different forms of antigen. Pavlakis G N, Gragerov A, and Felber B K. 2004 US Patent Application 2004/0241140 proposes that combinations of antigens applied at different sites and also at different times may increase protective immunity and suggest that using different forms of DNA sequentially or in combinations but applied at different sites may reproduce the improved immunogenicity obtained with other prime-boost vaccine combinations. They teach that combinations of vectors expressing different forms of antigens show improved immunogenicity especially when injected in different sites on the same mouse, compared to a mix of DNA vectors injected in the same site. The authors speculate that the efficiency of heterologous boosting of a DNA prime may be due to the different antigen presentation afforded by the heterologous vector or purified protein. The authors utilized secreted, cytoplasmic and proteosomal degraded versions of the antigen, and do not teach to use other targeting sequences, or to use a vector family or rationale strategy to facilitate determination of the optimal immunization cocktail.

Other investigators have also reported improved responses when two plasmids targeting an antigen to different cellular destinations were combined in immunization. Immunization with DNA vaccines using combinations of either secreted and cytoplasmic targeted antigen (Piechocki M P, Pilon S A, Wei W Z. 2001 *J Immunol*. 167:3367-3374), or cytoplasmic and ubiquitin conjugated forms of papillomavirus capsid genes (Liu W J, Zhao K N, Gao F G, Leggatt G R, Fernando G J P, Frazer I H. 2001 *Vaccine* 20: 862-869; Frazer I H. 2004 US Patent Application 2004/0241177]) or soluble or membrane anchored forms of HSV-2 glycoprotein D (Flo J 2003 Vaccine 21: 1239-1245) enhanced immune responses. These authors do not teach to use other targeting sequences, or to use a vector family to determine the optimal immunization cocktail.

Other investigators have reported no improvement in responses when two plasmids targeting an antigen to different cellular destinations were combined in immunization. For example, no enhancement of immune response was observed with a combination of cytoplasmic and endosomally targeted p55Gag (Marques E T A, Chikhlikar P, de Arruda L B, Leao I C, Lu Y, Wong J, Chen J S, Byrne B, August J T 2003 *J Biol. Chem.* 278: 37926-37936). However, when DNA vaccine plasmids targeting human immunodeficiency virus-1 gag to cytoplasmic or endosomal destinations were utilized in prime boost studies, endosome priming, cytoplasmic boosting gave immune responses that were similar or even stronger compared to endosome priming and boosting (and much stronger than cytoplasmic priming and boosting). The potential benefit of prime boost immunization with 2 plasmids with different targeting of the same antigen was not proposed or otherwise taught by the authors (Barros De Arruda L, Chickhlikar P R, August J T, and Marques E T A. 2004 *Immunol.* 112:126-33).

These studies teach that the optimal combination of plasmids for optimal immune protection will be antigen and delivery method specific, and will need to be determined for each antigen. The optimal presentation is also anticipated to be antigen and delivery specific. EP targets muscle cells and likely delivers antigens for immune presentation via cross presentation to APC. This may optimally require secreted and/or stable protein in the donor cell, along with cell death to attract and stimulate APC's. For Gene Gun, which targets dendritic cells, direct priming may be the dominant antigen presentation mode and proteosomal and/or endosomal targeted antigen, for enhanced MHCI or MHCII presentation, respectively, may be optimal. Combinations of plasmids, optimized for each modality, may ultimately provide superior protection. For example combinations of vectors expressing native, dendritic- and proteosomal-targeted SIV antigens provided superior protection in rhesus macaques (Rosati M, von Gegerfelt A, Roth P, ALicea C, Valentin A, Robert-Guroff M, Venzon D, Montefiori D C, Markham P, Felber B K, Pavlakis G N. 2005 *J Virol.* 79: 8480-8492); similar enhancement was observed with mixed plasmids encoding cytoplasmic and ubiquitin conjugated papillomavirus capsid genes (Liu et al. Supra, 2001). A rational method to determine the optimal presentation is not taught in the art.

As well, the art teaches that interpretation of existing mixed plasmid immunization results is uncertain, due the variations between vector backbone used in these examples. Targeting vectors, that allow fusion of a target antigen to different intracellular targeting sequences, such as those utilized above, or those described in Williams et al, Supra, 2001, and Bucht G, Sjolander K B, Eriksson S, Lindgren L, Lundkvist A, Elgh F. 2001 *Vaccine* 19: 3820-3829 are not optimally designed to determine immune responses to antigens targeted to various intracellular destinations. First, these vectors use standard typeII restriction enzyme cloning sites, for introduction of the antigen gene. The art teaches that small sequence variations between vector backbone can alter expression levels (Hartikka J, Sawdey M, Cornefert-Jensen F, Margalith M, Barnhart K, Nolasco M, Vahlsing H L, Meek J, Marquet M, Hobart P, Norman J, Manthorpe M. 1996 *Hum Gene Ther.* 7:1205-1217); different expression levels have been shown to influence the resulting immune response (Zinckgraf J W, Silbart L K 2003 *Vaccine* 21: 1640-1649). As well small peptide additions to recombinant proteins from cloning sites or peptide tags can alter the protein subcellular localization, even when these sequences do not contain targeting tags (Ramanathan M P, Ayyavoo V, Weiner D B. 2001 *DNA Cell Biol* 20: 101-105).

The targeting vectors of Williams et al, Supra, 2001 or Bucht et al, Supra, 2001, as well as other current DNA vaccine plasmids such as VR1012, also were constructed using standard typeII restriction enzyme cloning. This strategy, which utilizes nearest flanking useful restriction sites to move fragments into the vector ensures that the final vectors contain large amounts of extraneous sequences. These vectors do not comply with current WHO or FDA guidelines regarding content and elimination of extraneous materials. For example, VR1012 includes potentially detrimental sequences such as potentially recombinogenic transposon termini as an artifact of cloning the kanamycin resistance gene. Oligo-pyrimidine or oligo-purine sequences in a plasmid have been shown to increase dimer formation in a pUC plasmid, presumably through formation of unusual DNA structures such as a triple helix (Kato M. 1993 *Mol Biol Rep.* 18:183-187). VR1012 contains such sequences, as a polyG polyC tail used to join two fragments. Overall, a number of elements in bacterial derived sequences from prokaryotic plasmids have been shown to negatively affect gene expression in eukaryotic cells (Leite J P, Cousin C, Heysen A, D'Halluin J C. 1989 *Gene.* 82:351-356; Peterson D O, Beifuss K K, Morley K L. 1987 *Molec Cell Biol* 7:1563-1567) or bind eukaryotic transcription factors (Tully D B, Cidlowski J A. 1987 *Biochem Biophys Res Commun.* 144:1-10; Ghersa P, Whelan J, Pescini R, DeLamarter J F, Hooft van Huijsduijnen R. 1994 *Gene* 151: 331-332; Kushner P J, Baxter J D, Duncan K G, Lopez G N, Schaufele F, Uht R M, Webb P, West B L. 1994 *Mol. Endocrinol.* 8:405-407), ultimately decreasing the performance of the vectors. The presence of chi sites in plasmids have been shown to promote dimerization (Zaman M M, Boles T C. 1996 *J Bacteriol.* 178:3840-3845). Plasmid nicking may be associated with AT rich regions that 'breathe' and are susceptible to endogenous single stranded nucleases. Palindrome sequences are unstable, as are direct or inverted repeats and Z DNA forming sequences that are deleted or rearranged by the *E. coli* host. Unusual secondary structure DNA includes runs of potentially Z DNA-forming alternating pyrimidine/purine sequences (such as CpG sequences; Bichara M, Schumacher S, and Fuchs R P. 1995 *Genetics* 140:897-907), G-rich sequences that may form tetraplex structures, and oligopyrimidine or oligopurine sequences that may form triplex DNA.

Elimination of extraneous DNA is essential to reduce the chance of inclusion of such spurious binding sites. However, when DNA is eliminated, other problems can arise. For example, prokaryotic replication tends to terminate in the Cytomegalovirus (CMV) promoter. Termination is enhanced when the orientation of the origin is close to, and parallel with the CMV promoter. Interference is perhaps due to secondary structure, or fortuitous binding of bacterial protein. New minimized DNA vaccine vectors such as pVAX1 contain the CMV promoter and replication origin in close proximity due to size reduction; this vector produces replication intermediates, thus reducing the quality of plasmid produced in the bacterial host (Levy J. 2003 US Patent Application US2003180949).

Class IIS restriction enzymes provide the means to digest DNA molecules outside of the restriction endonuclease recognition sites, making it possible to introduce a site (by PCR) and to digest it, creating an overhanging terminus with specific address tag at any point. By combining this characteristic with gene amplification technology, class IIS sites in the PCR primers can digest DNA at any site, providing unique, non-palindromic overhanging ends, or specific address tags (Lebedenko E N, Birikh K R, Plutalov O V, Berlin YuA. 1991 *Nucleic Acids Res* 19: 6757-61). The Gene Self-Assembly process uses class IIS restriction enzymes to generate unique, non-palindromic overhanging termini that can ligate to only one other terminus in a complex mixture, thus assuring that each fragment ligates in the correct orientation to its correct partner, and none other. Nature Technology Lincoln Nebr. has developed a Gene Self Assembly vector, pWizBang, that can be used to create unique, non-palindromic address labels on a series of DNA molecules (such as blunt restriction fragments, or PCR amplicons), permitting a number of fragments (up to 32) to be instantly ligated into a single, complex construct at once. This step permits modular vector construction, and eliminates sequential sub-cloning. An advantage of this technique is that it is seamless—fragments can be joined at any base without the need for restriction sites at these loci (Hodgson, C, Zink, M A, Xu, G., U.S. Pat. No. 6,410,220) eliminating all extraneous sequences. However, Class IIS vector development methodologies have not been applied to creation of optimized DNA vaccine plasmids.

Even in view of the prior art, there remains a need for improved vectors that are minimized to eliminate extraneous DNA, organized to ensure high quality bacterial plasmid productivity and improved in vivo expression, improved innate and adaptive immune response induction, and designed to facilitate rapid and rationale evaluation of mixed plasmid immunization, such that this technology can be utilized to meet the efficacy threshold in humans and other mammals, birds or fish with a wide range of target antigens.

DISCLOSURE OF THE INVENTION

The invention relates to a family of eukaryotic expression plasmids, and immunization strategies, useful for obtaining improved genetic immunization.

An improved DNA vaccine vector family, with an identical backbone to limit variability, and seamless intracellular targeting cloning cassette which has demonstrated improved expression over state of the art vectors is disclosed. Critically, these vectors allow an antigen to be targeted to multiple intracellular destinations, without alteration of flanking vector or gene sequences. The vectors were constructed by simultaneously joining six fragments, using Gene Self-Assembly technology which eliminates the need for additional sequences at the junction between fragments used in a vector assembly. All plasmid elements have been optimized and minimized to comply with FDA guidelines regarding content and elimination of extraneous materials. The resulting vector is much smaller than existing vectors such as VR1012 (5 kb, versus 3-3.5 kb for the pDNAVACCUltra vectors) and drives higher levels of target gene expression. Incorporation of an optimized kanR gene-pUC origin orientation, as well as a novel rationally designed RNAII replication origin mutation, results in 2 fold improved plasmid productivity. These vectors are designed to facilitate high throughput cloning applications, and allow simultaneous cloning into multiple vectors that feature various intracellular targeting destinations for the protein product. The cloning requires no additional bases, such as a restriction enzyme site, to be present in the vector. Thus, the variability between vectors imposed by additional bases required for traditional cloning is eliminated.

As well, the vectors can be used in new immunization strategies such as "mixed presentation immunization", wherein an immune response to a target antigen is enhanced by immunization with a plasmid cocktail, which combines 2 or more plasmids each targeting the antigen to different intracellular destinations.

As well, the vectors encode expressed RNA sequences (RNA elements), in addition to the optimized protein antigen expression element. These expressed RNA sequences add additional functionality to the vector to customize and enhance immune responses. For example, the RNA elements may be immunostimulatory, promote or repress apoptosis, direct cell death to necrotic pathways, enhance plasmid nuclear localization and promoter expression, or otherwise alter cell expression. The RNA elements may encode a single stranded RNA, a double stranded RNA, a hairpin RNA, a microRNA, a RNA aptamer or a ribozyme or combinations thereof. Due to the small size of an RNA expression element (100-500 bp), multiple elements can be included within a single plasmid. Since RNA does not induce adaptive immune responses against itself, the response to RNA containing vectors is not dependent on prior exposure of the patient, and can therefore be utilized repeatedly, without inducing immune responses to the vector backbone.

As well, the vectors can be used in a new immunization algorithm, RapidVACC, to rapidly screen for possible routes of presentation that provide an optimized mix of immunostimulatory sequences, presentation modes, and antigens to bestow protection. Targeted antigen presentation using immunostimulatory DNA vaccine plasmids, alone or in plasmid combinations optimized for MHCI and MHCII presentation (mixed presentation immunization), is utilized to provide improved immune responses. The optimal presentation will be antigen and delivery route specific. Combinations of plasmids, optimized for each modality, may ultimately provide superior protection.

BRIEF SUMMARY OF THE INVENTION

It is a purpose and/or objective of the present invention to provide DNA vaccine plasmids for production of immune responses through DNA vaccination. Another disclosure is improved DNA vaccine plasmid compositions that, compared to plasmids defined in the art such as VR1112, pVAX1, pVC0396, pCMVkm2, or pCOR vectors, or their derivatives, are improved by: increased eukaryotic expression of target antigen by incorporation of a novel chimeric SV40 enhancer-CMV promoter; increased eukaryotic expression by optimization of elements upstream of the eukaryotic promoter; increased eukaryotic expression by addition of RNA export signals; smaller size by elimination of all extraneous sequences such as additional sequences flanking prokaryotic origin or antibiotic resistance gene present in other vectors. These sequences are present in existing vectors as a consequence of using the nearest useful restriction sites for creation of the vectors. This includes removal of potentially recombinogenic transposon termini present in other vectors, for example VR1012; smaller size by creation of novel short leader-intron to replace large CMV leader intron 1; smaller size by creation of novel short eukaryotic transcription terminator to replace large bovine Growth hormone terminator or rabbit β globin terminator; improved yield and integrity during bacterial production by inclusion of transcriptional terminators flanking prokaryotic region to protect against target antigen expression; improved integrity during bacterial production by removal of additional sequences, such as polyG polyC tails used in cloning fragments in VR1012, that may promote dimer or concatamer formation during bacterial propagation; improved yield and integrity during bacterial production by optimization of the kanamycin resistance gene, origin of replication orientation; improved yield during bacterial production by inclusion of a novel enhanced replication origin compared to the pUC or pMM1 origin; precise cloning and expression of antigens without extraneous sequences by using TypeIIS enzymes for cloning rather than traditional TypeII enzymes; flexible targeting of antigens to various intracellular destinations, without perturbation of the flanking vector or gene sequences by using TypeIIS enzymes for cloning. VR1012, pVAX1, pVC0396, pCMVkm2, or pCOR vectors do not allow antigen targeting.

Yet another objective and/or purpose of the invention is new immunization methods to improve the efficacy of DNA vaccination. The vectors of the current invention are used to improve the effectiveness of DNA vaccines by: increasing target gene expression compared to DNA vaccine plasmids defined in the art; and facilitating new immunization methods that require flexible targeting of antigens to various intracellular destinations such as: determination of the optimal antigen intracellular targeting to use in DNA priming; determination of the optimal antigen intracellular targeting to use in DNA boosting; determination of the optimal antigen intracellular targeting to use in DNA prime, DNA boost immunization; determination of the optimal combination of antigen intracellular targeting plasmids to use in DNA priming; determination of the optimal combination of antigen intracellular targeting plasmids to use in DNA boosting; determination of the optimal combination of antigen intracellular targeting plasmids to use in DNA prime, DNA boost immunization.

Yet another objective and/or purpose of the invention are novel expressed RNA-containing DNA vaccine vector backbones to improve the efficacy of DNA vaccination. The vector backbones of the current invention encode expressed RNA sequences, in addition to the optimized protein antigen expression element. These expressed RNA sequences add additional functionality to the vector such as; immunostimulatory RNA; apoptosis promoting RNA; apoptosis repressing RNA; necrotic cell death promoting RNA; plasmid nuclear localization promoting RNA; promoter expression promoting RNA; ligand binding RNA; gene inactivating short hairpin RNA; antigen cross presenting promoting RNA; or other RNAs that alter cell expression to customize and enhance immune responses. The RNA elements may encode single stranded RNAs, double stranded RNAs, hairpin RNAs, micro RNAs, RNA aptamers or ribozymes or any or all combinations thereof. Due to the small size of an RNA expression element (100-500 bp), multiple elements can be included within a single plasmid; in the case of multiple plasmid immunization, different RNA elements may be included on each plasmid. Since RNA does not induce adaptive immune responses to itself, the response to RNA containing vectors is not dependent on prior exposure of the immunized individual, and can therefore be utilized repeatedly, without inducing immune responses to the vector backbone.

In summary, the vectors combine reduced size and sequence content (which improves regulatory compliance and potency) with improved performance in production, transcription, presentation targeting, yield, integrity, genome recombination propensity (safety), and regulation of innate immune responses by RNA elements.

Further objects and advantages of the invention will become apparent from a consideration of the drawings and ensuing description.

BRIEF DESCRIPTION OF THE DRAWING FIGURES

FIG. 1. shows the gene Self Assembly Vector pWiz-Bang 2.0.

FIG. 2. shows pDNAVACCultra plasmids.

FIG. 3. illustrates a method for directional amplification and cloning of cDNA sequences into pDNAVACC vectors.

Figure 4:
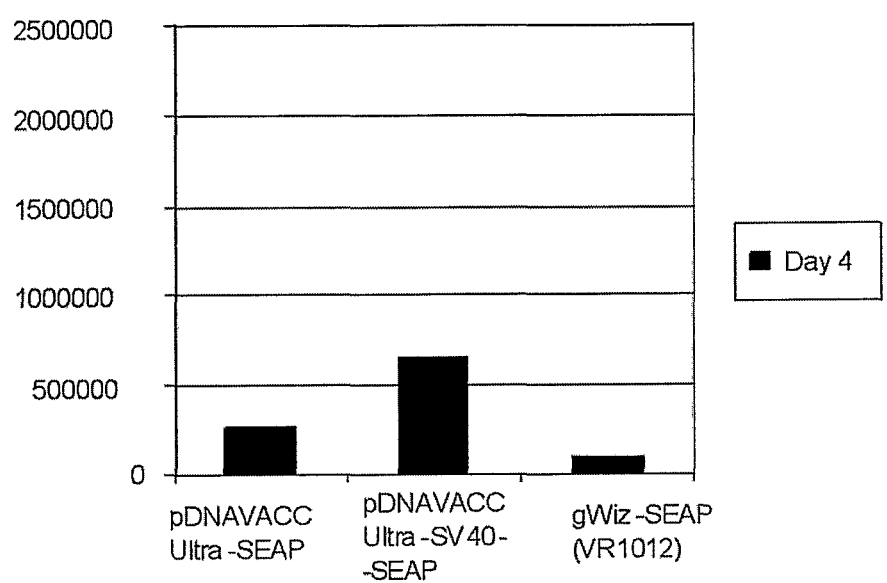

FIG. 4. shows in vivo expression from pDNAVACC plasmids.

FIG. 5. shows stuffer sequences for the vectors.

Figure 6:
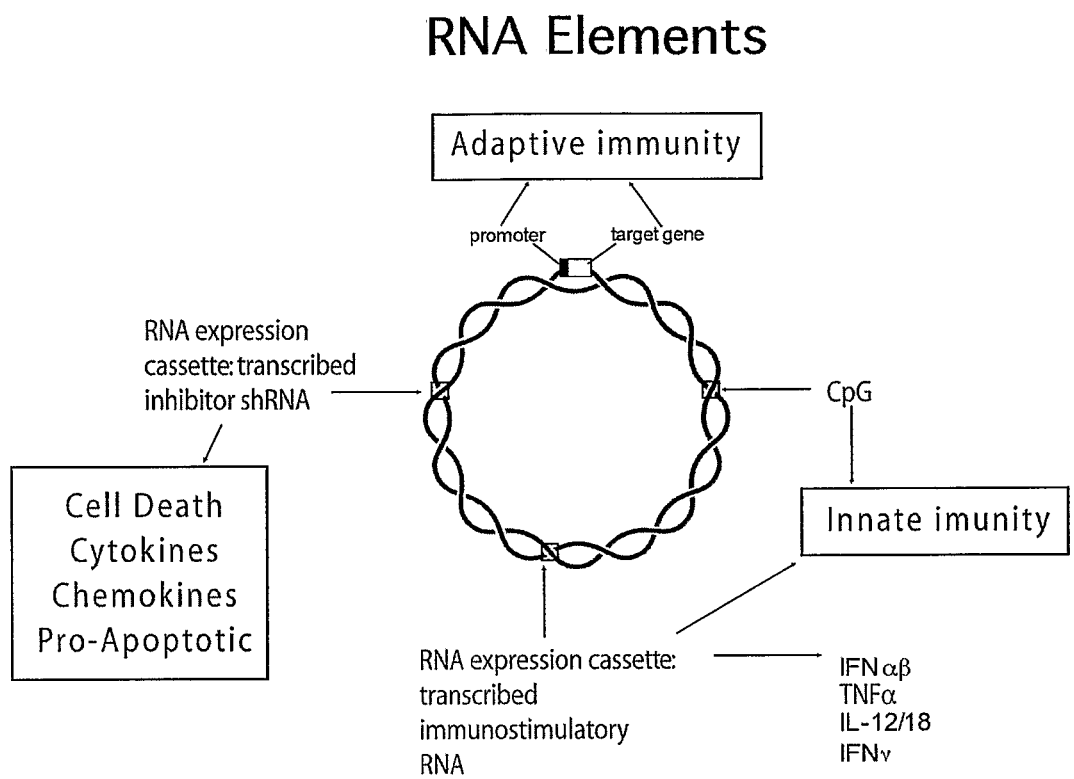

FIG. 6. shows vector incorporated RNA elements.

Figure 7:
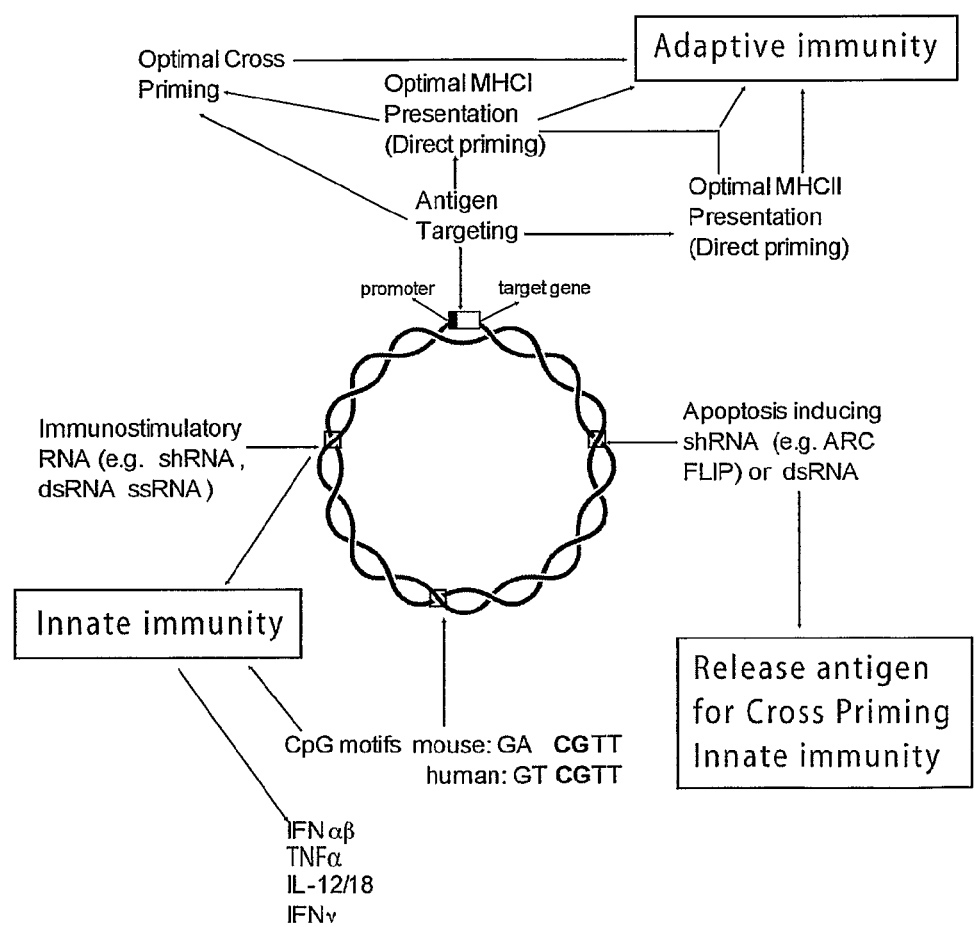

FIG. 7. illustrates the application of immunostimulatory DNA vaccines.

Figure 8:
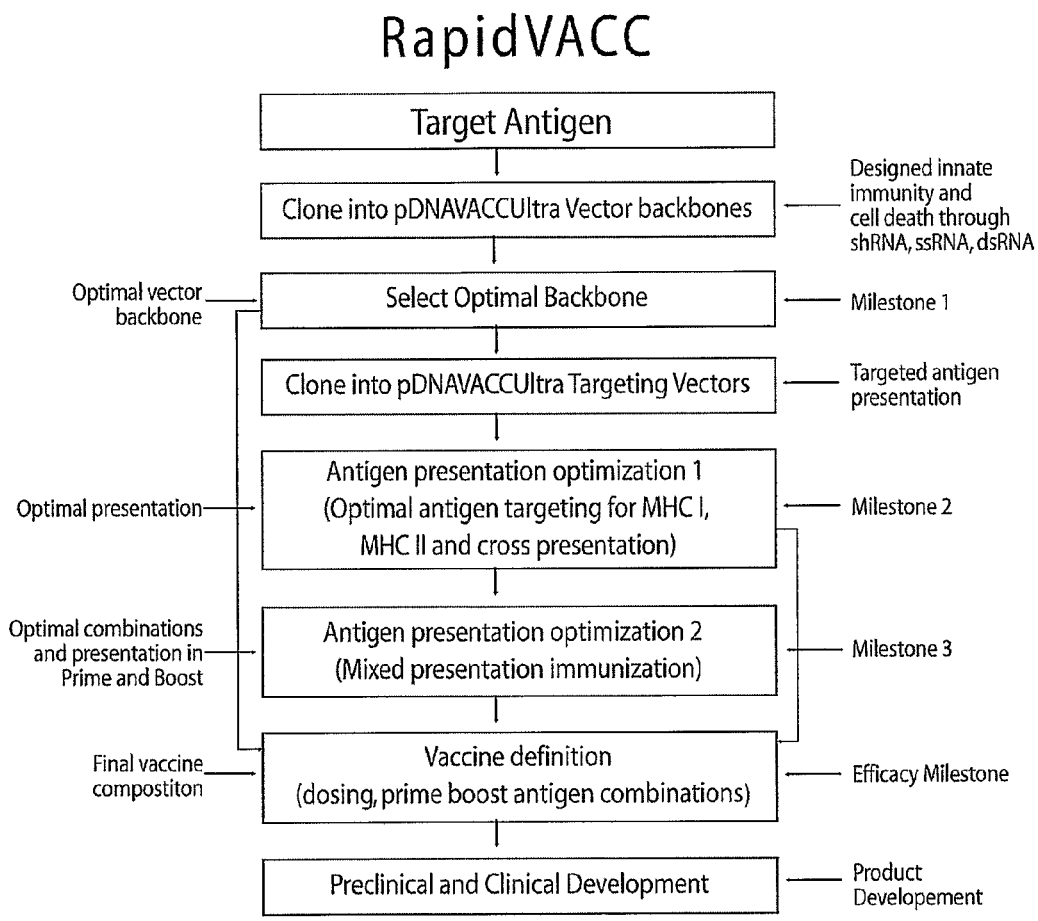

FIG. 8. illustrates the RapidVACC algorithm flowchart.

Figure 9:
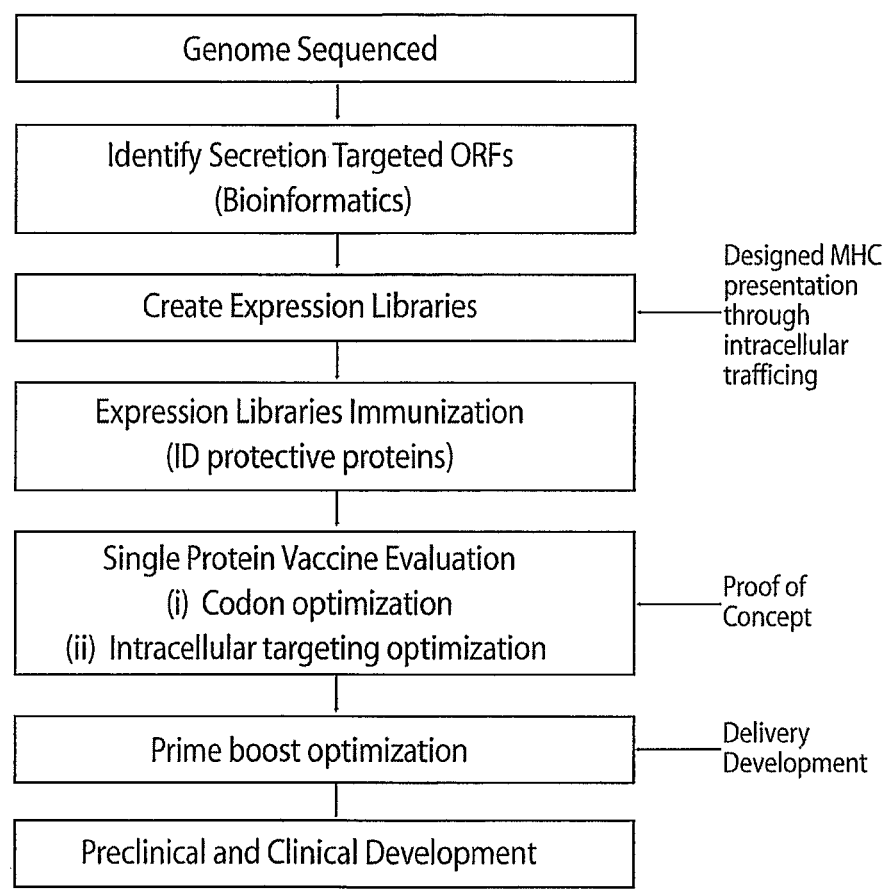

FIG. 9. illustrates the RapidVACC algorithm flowchart for identification of protective antigens from sequenced genomes.

Figure 10:
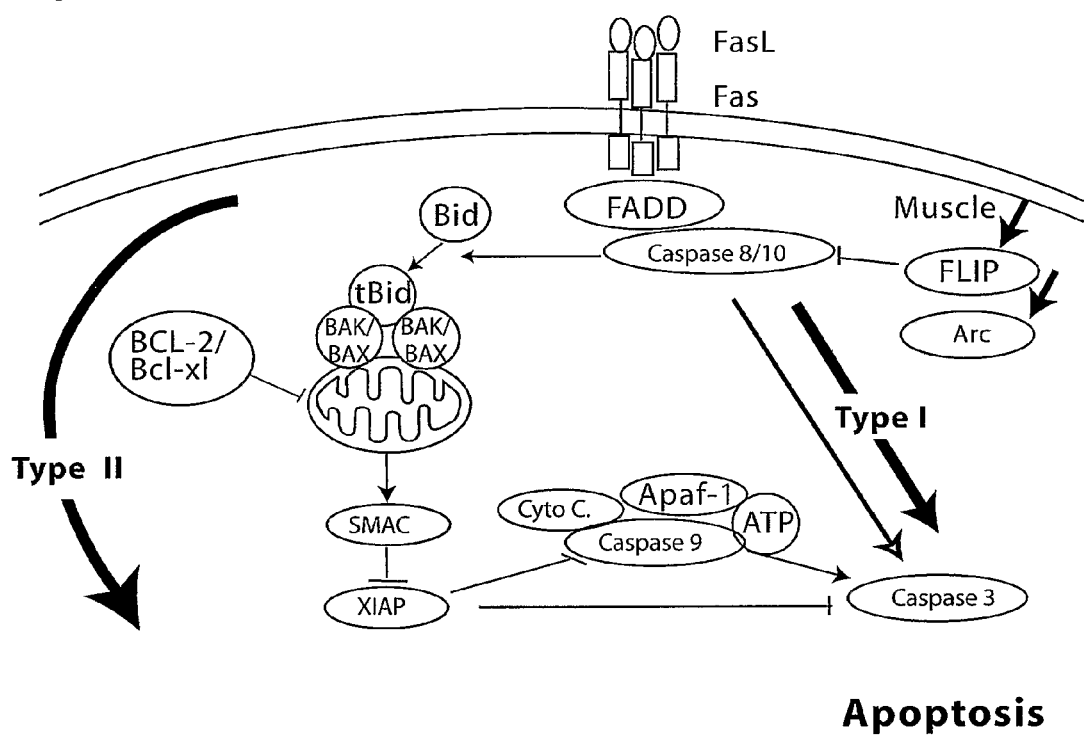

FIG. 10 shows targets for RNA elements that can be utilized to promote or repress apoptosis.

Table 1: Optimization of origin composition and orientation in pDNAVACC plasmid

Table 2: Fibroblast activity of chimeric promoters

Table 3: Antigen Presentation Pathway Targeting molecules

Table 4: Replication origins

Table 5: Immunostimulatory RNA element induced TNFα production in RAW 264.7 cell line (36 hrs post transfection)

Table 6: Immunostimulatory RNA element induced TNFα production in RAW 264.7 cell line (15 hrs post transfection)

DETAILED DESCRIPTION OF THE INVENTION

Turning now to the drawings, FIG. 1. shows use of the Gene Self Assembly Vector pWiz-Bang 2.0. (a) design primers to create 4 bp overlaps, amplify module, clone into linear vector, sequence verify; and (b) release with AarI digestion, ligate fragments, creating the final gene or construct in a single step.

In FIG. 2, the pDNAVACCultra plasmid backbone is shown. (a) map of pDNAVACCultra5-EGFP; (b) map of pDNAVACCultra2-SV40 (NTC7142); (c) map of pDNAVACCultra5-EGFP-mU6 RNA expression element containing plasmid; and (d) map of pDNAVACCultra5-EGFP-SV40-mU6 RNA expression element containing plasmid.

In FIG. 3, the method for directional amplification and cloning of cDNA sequences into pDNAVACC vectors is outlined. (a) plasmid containing two unique address tags, created by digestion with class IIS enzymes located between cuts; and (b) typical primer, containing a class IIS enzyme recognition signal (SapI), at least one intervening nucleotide, and an overlapping region with a unique, non-palindromic sequence (GGG, the address tag in this example).

In FIG. 4, in vivo expression from pDNAVACC plasmids is shown. in vivo expression of SEAP driven by pDNAVACCultra-SEAP vector, pDNAVACCultra-SV40-SEAP vector, or gWIZ-SEAP.

In FIG. 5, the high throughput intracellular targeting cloning sites are illustrated for: (a) pDNAVACCultra1 (secreted-endosome); (b) pDNAVACCultra2 (secreted); (c) pDNAVACCultra3 (secreted-membrane anchored); (d) pDNAVACCultra4 (proteosome); (e) pDNAVACCultra5 (native); (f) pDNAVACCultra6 (membrane anchored); (g) pDNAVACCultra7 (endosome); and (h) pDNAVACCultra8 (secreted-cross presentation).

In FIG. 6, vector incorporated RNA elements are shown

In FIG. 7, the application of immunostimulatory DNA vaccines is illustrated

In FIG. 8, the RapidVACC flowchart is shown for development of a single antigen DNA vaccine.

In FIG. 9, the RapidVACC flowchart for identification of protective antigens from sequenced genomes is illustrated.

In FIG. 10 targets for RNA elements that can be utilized to promote or repress apoptosis are shown. Arrows denote ARC and FLIP, which are enriched in skeletal muscle Definitions adjuvant: Includes nucleic acid adjuvants (e.g. immunostimulatory CpG sequences, expression vectors of cytokines, chemokines or other molecules such as cell death promoters (e.g. herpes thymidine kinase) and chemical adjuvants which are compounds that can enhance, prolong or otherwise modulate antigen-specific immune responses when administered with a vaccine antigen. These are well known in the art and are included herein by reference (see Williams et al, 2001 for examples)

APC: Antigen Processing Cell, for example, langerhans cells and dendritic cells

BAC: bacterial artificial chromosome ccc: Covalently Closed Circular costimulatory molecules: costimulatory plasmids (e.g. IL12) or molecules, cell death inhibitors (e.g. antiapoptotic proteins) or enhancers as know in the art and included herein by reference cmv: cytomegalovirus delivery methods: methods to deliver gene vectors (e.g. poly(lactide-co-glycolide) (PLGA), ISCOMs, liposomes, niosomes, virosomes, chitosan, and other biodegradable polymers, electroporation, sonoporation, ultrasound, gene gun, needle free biojector, liposomes, microparticles, microspheres, nanoparticles, virosomes, bacterial ghosts, bacteria, attenuated bacteria, etc) as know in the art and included herein by reference dsRNA: double stranded RNA Gene Self-Assembly: The Gene Self-Assembly process uses class IIS restriction enzymes to generate unique, non-palindromic overhanging termini that can ligate to only one other terminus in a complex mixture, thus assuring that each fragment ligates in the correct orientation to its correct partner, and none other GPI: glycosylphosphatidylinositol HA: hemagluttinin immune response: antigen reactive cellular (e.g. antigen reactive T cells) or antibody (e.g. antigen reactive IgG) responses intracellular targeting: directing a target antigen to either an inter or intracellular destination, or the antigen presentation pathway as described above, using a targeting sequence as described above with a non limiting list summarized in Table 3 mixed presentation immunization: immunization with a plasmid cocktail, or a plasmid-protein cocktail, which combines 2 or more plasmids each targeting the antigen to different intracellular destinations using a targeting sequence as described above with a non limiting list summarized in Table 3, with or without the corresponding protein antigen NP: nucleoprotein PCR: Polymerase Chain Reaction pDNA: Plasmid DNA plasmid: plasmids, cosmids, bacterial artificial chromosomes (BACs), bacteriophages, viral vectors and hybrids thereof pUC origin: pBR322-derived origin, with G to A transition that increases copy number at elevated temperature RapidVACC: vaccine development process that involves determination of optimal plasmid backbone and/or presentation of protective antigen(s) using targeting plasmid immunization methods disclosed herein combined with antigen identification methods known in the art RNA element: An expression cassette containing an expressed RNA sequence. The promoter may be a PolI, PolII or PolIII promoter, and the expressed RNA may be a single stranded RNA, double stranded RNA, hairpin RNA, microRNA, RNA aptamer or a ribozyme shRNA: short hairpin RNA siRNA: short inhibitory RNA ssRNA: single stranded RNA target antigen: immunogenic protein or peptide epitope, or combination of proteins and epitopes, against which a immune response can be mounted. Target antigens may by derived from a pathogen for infectious disease applications, or derived from a host organism for applications such as cancer, allergy, or autoimmune diseases. Target antigens are well defined in the art. Some examples are disclosed in Williams et al, 2001 and included herein by reference targeting molecules: both intracellular targeting sequences and antigen presentation pathway targeting molecules as described above with a non limiting list summarized in Table 3

$T_H1$: T helper 1

$T_H2$: T helper 2

TLR: Toll Like Receptor vector: A gene delivery vehicle, including viral (e.g. alphavirus, poxvirus, adenovirus, adenovirus related virus, etc) and nonviral (e.g. plasmid, midge, transcriptionally active PCR fragment, minicircles, bacteriophage, etc) vectors. These are well known in the art and are included herein by reference The invention relates to compositions and methods for protein expression and genetic immunization. The invention is practiced in the expression of gene products in eukaryotic cells, for the purpose of genetic immunization, gene therapy, recombinant protein production, or other biotechnological applications. The invention applies to such use of ccc recombinant DNA molecules such as plasmids, cosmids, BACs, bacteriophages, viral vectors and hybrids thereof (herein collectively referred to as plasmids).

DNA vaccine plasmids described in the art are not optimal with suboptimal expression, additional nonessential DNA, nor do they facilitate high throughput projects, or flexible targeting of antigens to various intracellular destinations. These deficiencies are critical, since several incremental improvements in the vectors could result in large differences in expression levels, quality of immune responses and ultimately protective immunity.

Vector Construction Preferred Embodiments

In one preferred embodiment for creation of DNA vaccine plasmids cloning is performed using type IIS restriction enzymes. Here we disclose the development of an advanced Gene Self Assembly vector, pWizBang2.0, that uses the enzyme AarI to generate 4-base overhanging termini (FIG. 1). Up to 121 fragments can be unambiguously joined using this method. We have demonstrated the utility of this vector for complex cloning projects by creation of a family of modular DNA vaccine vectors (FIG. 2) that are uniquely designed to eliminate all extraneous sequences, facilitate high throughput vaccine discovery projects, and seamless fusion of a target antigen to intracellular targeting sequences.

The success rate of cloning (>90%) suggest pWizBang2.0 can generally be utilized for highly complex cloning projects. The ability to sequence input fragments before gene construction provides assurance that the final constructs will not contain mutations caused by faulty oligonucleotide primers (common), or from PCR enzymes (rare). The process requires oligonucleotide primers of high integrity, together with a high-fidelity polymerase enzyme (such as Pfu DNA polymerase) that does not add extra bases (if gene amplification is used).

Target Gene Cloning Preferred Embodiments

In one preferred embodiment for cloning antigens into DNA vaccine plasmids, cloning is performed using type IIS restriction enzymes. By way of example, pDNAVACCultra vectors are shown in FIG. 2. The vectors facilitate cloning of genes or epitopes of interest seamlessly downstream of the desired intracellular targeting gene leader cassette by using TypeIIS enzyme cloning methodologies. The cloning site is designed for high throughput cloning applications, and is compatible between multiple vectors, allowing several different intracellular targeted gene constructs to be made in one step (FIG. 3).

DNA Vaccine Plasmid Preferred Embodiments

In one preferred embodiment for immunization, immunization is performed using a pDNAVACCUltra vector. By way of example, pDNAVACCultra vectors are shown in FIG. 2. The prokaryotic region (replication origin and Kanamycin resistance gene) is flanked by prokaryotic transcriptional terminators to improve stability and yield with a broad range of target genes. Unique restriction sites flank the prokaryotic modules, to allow easy modifications (i.e. replacement of KanR cassette with repressor titration cassette). All plasmid elements have been optimized and minimized to comply with current WHO and FDA guidelines regarding content and elimination of extraneous materials. The resulting vector is much smaller than existing vectors such as VR1012 (5 kb, versus 3-3.5 kb for the pDNAVACC vectors) yet drives higher levels of expression in vitro and in vivo.

The functionality of each element has been validated by comparison of transient expression levels in cell lines transfected with either the pDNAVACC plasmids or a series of plasmid swaps replacing each element with the corresponding element from the Vical VR1012 DNA vaccine vector. Extensive optimization of the orientation and composition of the prokaryotic portion of the plasmid unexpectedly resulted in improved productivity and stability in bacterial culture and improvement of the in vitro and in vivo expression, compared to existing DNA vaccine plasmids (Table 1, FIG. 4).

TABLE 1

Optimization of origin composition and orientation in pDNAVACC plasmid

| Origin Configuration* | Relative Copy Number at 37° C.** | In vitro expression*** | Replication Intermediates |
|---|---|---|---|
| Configuration 1: ▮ T▶pUC origin T◀KanR T ▮ | 1.0x (pDNAVACC-EGFP) | ++ | Detected |
| Configuration 1: ▮ T◀Ultra origin T◀KanR T ▮ | 1.5x | NA | NA |
| Configuration 2: ▮ T pUC origin▶T◀KanR T ▮ | 0.7x | NA | NA |
| Configuration 3: ▮ T▶pUC origin KanR▶TT ▮ | 1.8x | NA | NA |
| Configuration 3: ▮ T◀Ultra origin KanR▶TT ▮ | 2.0x (pDNAVACC Ultra-EGFP) | +++++ | ND |

*T = Transcriptional terminator TT = Tandem dual transcriptional terminators NA = Not assayed ND = None detected
**Relative to pDNAVACC-EGFP
***Expression of EGFP in eukaryotic cell lines, from lowest + to highest +++++

The minimalized and optimized individual components from above showed equivalence to the corresponding region from the VR1012 vector in the vector swap experiments. Expression levels from the CMV and NVL-3 promoters are unexpectedly affected by the orientation of the kanamycin resistance gene, with dramatically higher expression when the kanamycin gene promoter is distal to the eukaryotic promoter (Tables 1 and 2). Unexpectedly, the combination of these minimalized and optimized elements in the pDNAVACCUltra vector are synergistic, resulting in an overall improved plasmid expression in eukaryotic cells (Tables 1 and 2).

TABLE 2

Fibroblast activity of chimeric promoters

| Promoter Configuration** | Expression* |
|---|---|
| CMV | ++ |
| CMV (ultra) | +++++ |
| SV40-CMV | +++ |
| SV40-CMV (ultra) | +++++ |
| NVL-3 | + |
| NVL-3 (ultra) | +++ |
| SV40-NVL-3 | +++ |
| SV40-NVL-3 (ultra) | ++++ |
| NFκB-NVL-3 | ++ |
| NFκB-SV40-NVL-3 | ++ |
| NFκB-CMV | ++++ |
| NFκB-SV40-CMV | +++ |

*Expression from lowest + to highest +++++
**Ultra refers to optimal orientation of kanR gene In another preferred embodiment for immunization, a pDNAVACCUltra vector incorporating a chimeric promoter is utilized. Novel chimeric promoters are disclosed, combining which further increases expression of target antigens (FIG. 4).

A novel chimeric promoter, wherein the SV40 enhancer is fused upstream of the CMV promoter was unexpectedly found to dramatically increase in vivo expression (FIG. 4). It is unknown if the improved expression results from increased transcriptional activity and/or improved nuclear localization of the plasmid. The latter is a possibility since regions of the SV40 enhancer has been demonstrated to facilitate nuclear localization of DNA vaccine plasmids in muscle cells, with dramatically enhanced target protein expression (Dean et al, Supra, 1999), as predicted by Graessman M, Menne J, Liebler M, Graeber I, and Graessman A 1989 *Nucleic Acids. Res.* 17: 6603-6612. Binding sites for NFKB (Mesika A, Grigoreva I, Zohar, M, Reich, Z. 2001 *Molecular Therapy* 3: 653-657) and smooth muscle-specific transcription factor SRF (Zohar M, Mesika A, Reich Z. 2001 *BioEssays* 23:1176-1179) also mediates this effect. However, the improved expression must be more complex than nuclear localization alone, since the NFKB-SV40-CMV enhancer construct did not perform as well as SV40-CMV alone when incorporated into DNA vaccine plasmids.

Bacterial Production of Plasmid DNA Preferred Embodiments

In one preferred embodiment for bacterial production of plasmid DNA, the orientation of elements in the plasmid are optimized to maintain viability of the cell line. We teach the novel observation that cryopreservation viability must be evaluated during plasmid optimization. Reduced viability in glycerol stocks that was unexpectedly observed with plasmids incorporating the SV40 enhancer. This was plasmid specific and pDNAVACCUltra vector developed herein has a high glycerol stock viability. We found that determining the optimal orientation of elements within a plasmid to maintain cell line viability is not taught in the art, and we teach to determine this by altering the orientation of elements in the vector and testing for viability.

In another preferred embodiment for bacterial production of plasmid DNA, the orientation of elements in the plasmid are optimized to maintain or enhance plasmid quality. DNA quality and yield are affected by the organization of elements, as well as the specific elements included (e.g. IRES, CMV promoter). We demonstrate herein that it is essential to evaluate plasmid quality during development of a therapeutic plasmid. We teach that such evaluation needs to assay 1) Replication intermediates 2) dimerization and 3) % supercoiling over the number of generations that the plasmid may be propagated during production. The pDNAVACCUltra vector developed herein has a high degree of stability and quality with respect to these attributes.

Replication intermediates: Replication tends to terminate in internal ribosome entry sites (IRES) [e.g. encephalomyocarditis virus (EMCV) ires] and eukaryotic enhancer repeat regions [e.g. Cytomegalovirus (CMV) promoter, or Rous Sarcoma Virus (RSV) LTR]. Termination is enhanced when the orientation of the origin is close to, and parallel with the CMV promoter. Interference is perhaps due to secondary structure, or fortuitous binding of bacterial protein. This phenomenon is only seen in high copy plasmids; the same arrangement on low copy plasmids does not make detectable intermediates (Levy, Supra, 2003). The presence of the replication intermediate is readily observed as an extra small band in purified plasmid preparations. These intermediates reduce plasmid yield (copy number) due to aborted replication cycles, plasmid purity, and increases purification costs necessary to remove this related impurity. Failure to remove replication intermediates will decrease the purity and potency of the final plasmid. The pDNAVACCultra plasmids do not place the origin of replication in proximity to the CMV promoter, and produced high quality supercoiled monomer DNA, that did not give rise to detectable replication intermediates or concatamers. Replication intermediates were unexpectedly observed if the orientation of the kanamycin resistance gene was reversed. Inclusion of the SV40 enhancer also unexpectedly increases the amount of replication intermediate formed. The art teaches that the orientation of the kanamycin resistance gene in these vectors should not affect replication intermediate formation, and that replication intermediates should not be observed with either orientation. The basis for the novel orientation dependence of the kanamycin gene with respect to replication intermediate formation is unknown. We teach that the optimal orientation of elements to reduce replication intermediates is not taught in the art, and can be reduced by altering the orientation of elements in the vector and testing for replication intermediates.

Dimerization sequences: Most plasmid recombination is independent of RecBCD, and is mediated by the RecF pathway, which requires RecA, along with other gene functions. RecBCD is the major enzyme responsible for degradation of linear DNA in *E. Coli*. RecBCD degradation is arrested at Chi sites. RecBCD directed recruitment of RecA to chi sites stimulates homologous recombination. The presence of chi sites in plasmids have been shown to also promote RecF independent recombination by the RecBCD pathway in recA+ sbcB+ (wild type) cells (Zaman and Boles, Supra 1996). Oligo-pyrimidine or oligo-purine sequences in a plasmid have been shown to increase dimer formation in a pUC plasmid, presumably through formation of unusual DNA structures such as a triple helix (Kato, Supra 1993). The pDNAVACCultra vectors do not contain such sequences, and show very low levels of dimerization.

Sequences detrimental to plasmid quality: Certain sequences promote poor supercoiled content (i.e. significant percent of total plasmid is open circular). Unfortunately, the presence of such sequences in a plasmid needs to be empirically determined. Nicking may be associated with AT rich regions that 'breathe' and are susceptible to endogenous single stranded nucleases. Palindrome sequences are unstable, as are direct or inverted repeats and Z DNA forming sequences that are deleted or rearranged by the *E. coli* host. Unusual secondary structure DNA includes runs of potentially Z DNA-forming alternating pyrimidine/purine sequences (such as CpG sequences), G-rich sequences that may form tetraplex structures, and oligopyrimidine or oligopurine sequences that may form triplex DNA. The pDNAVACCultra vectors are devoid of sequences that promote nicking.

In yet another preferred embodiment for bacterial production of plasmid DNA, the orientation of elements in the plasmid are optimized to increase plasmid copy number. We teach that plasmid yield is unexpectedly and dramatically altered by orientation of the prokaryotic origin and kanR gene relative to each other in the same vector backbone. In general, the art teaches the replication origin needs to be protected from read-through transcription from adjacent genes to prevent plasmid destabilization or reduced copy number (Eastman, E M, Durland R H. 2000 U.S. Pat. No. 6,103,470; Engels P, Meyer P. 1993 *Biotechniques*. 14: 324-325). The optimal orientation determined herein protects the origin from transcriptional readthrough, by divergent transcription of the origin and kanR gene, as well as inclusion of dual transcriptional terminators after the kanR gene.

RNA Producing DNA Vaccines Preferred Embodiments

In one preferred embodiment to improve immune responses, immunization is performed using an RNA element-containing DNA vaccine vector (FIG. 6). We contemplate utilizing DNA vaccine vectors containing expressed (amplifiable) ssRNA, shRNA and dsRNA sequences, to further improve expression and/or immune responses as described below. Preferably, the RNA sequences are immunostimulatory, are selectively pro- or anti-apoptotic, or act to improve expression from the plasmid. The shRNA and dsRNA containing vector backbones will not induce adaptive immune responses (i.e. reuseable vectors unaffected by prior immune exposure); this is a significant advantage over alternative vectors such as alphaviral replicon vaccines. The vectors can provide a range of immunostimulatory and apoptotic activities (FIG. 7) theoretically allowing the optimal to be selected using RapidVACC (FIG. 8); different optimal combinations are expected for different delivery methods. These vectors form the basis for the first step of the RapidVACC vaccine development platform, wherein cell death and innate immune stimulation is optimized.

RNA polymerases I, II or III responsive promoters can also be utilized to make RNA. Preferably, RNA elements utilize RNA polymerases III promoters for expressions.

The incorporation of RNA elements into a DNA vaccine plasmid is not taught in the art. RNA elements provide a novel and enabling solution to the poor immune response induction associated with DNA vaccination, without the need to include immunogenic proteins in the plasmid backbone to induce cell death or innate immune responses (as with alphavirus replicons or flagellin producing plasmids). As well, RNA elements provide a solution to the cost, regulatory and safety issues associated with inclusion of heterologous adjuvants with the vaccine (such as immunostimulatory RNA or cytokines or chemokines, or gene inhibiting synthetic siRNA) since these can now be produced or induced by the plasmid backbone strictly in the cells containing the DNA vaccine plasmid (FIG. 7). RNA elements offer an unprecedented flexibility since vectors can contain multiple RNA elements, the optimal combination of which can be rapidly determined for each antigen/delivery using a rationally designed algorithm (RapidVACC; FIG. 8). These elements can be used in combinations to optimize immune responses. The RNA elements may be immunostimulatory, promote or repress apoptosis, direct cell death to necrotic pathways, enhance plasmid nuclear localization and promoter expression, or otherwise alter cell expression. The RNA elements may encode single stranded RNA, double stranded RNA, hairpin RNA, microRNA, RNA aptamer or ribozymes or combinations thereof. Due to the small size of an RNA expression element (100-500 bp), multiple elements can be included within a single plasmid. Since RNA does not induce adaptive immune responses, the response to RNA containing vectors is not dependent on prior exposure of the animal or human subject, and can therefore be utilized repeatedly, without inducing immune responses to the vector backbone.

The inclusion of RNA elements in a DNA vaccine backbone is a novel solution to the poor antigen expression or immunogenicity problem. While the prior art teaches that various immunostimulatory RNAs can induce interferon and other adaptive immune responses, and improve responses to DNA vaccines, the inclusion of such elements in the vaccine backbone was not contemplated. As well, while DNA vaccines are improved by the inclusion of vector expressed protein adjuvants (e.g. flagellin) pro apoptosis proteins (alphaviral replicon or mutant caspases) or anti apoptosis proteins, these approaches are limiting since the vector backbone now either induces adaptive immune responses to the encoded protein or contains human proteins (safety considerations). As well, due to the small size of RNA elements, multiple elements (functionalities) can be included in the vector backbone, to provide unprecedented flexibility in immune response modulation that is not contemplated or taught in the art. This novel, new and unsuggested combination of elements (RNA elements with antigen expression) enables development of cost effective, safe, multiple use DNA vaccines that improve and customize immune responses. The use of shRNA expressing vectors to augment immune response to DNA vaccine vectors is also new and is not contemplated in the art. While shRNA plasmids designed for gene silencing have been shown to induce interferon response (Pebemard S. Iggo R D. 2004 *Differentiation* 72: 103-111) and similar immune system activation has been observed with siRNA (Marques J T, Williams B R G. 2005 *Nature Biotech* 23: 1399-1405) this prior art teaches away from the invention, since the investigators view innate immune response to siRNA or shRNA as a problem for commercialization of gene knockdown vectors. As well, clearly, an investigator skilled in the art would not anticipate this new development, since the extensive prior art from both the highly crowded DNA vaccine and shRNA fields does not teach to use RNA elements to improve DNA vaccination. Once conceived as disclosed herein, this previously unsuggested modification to the DNA vaccine backbone (linkage of RNA elements into DNA vaccine backbones) teaches a number of new and unexpected results that will be clear to an investigator skilled in the art. For example, the long felt but unsolved need to improve immune responses to DNA vaccine vectors, without inclusion of human proteins such as plasmid produced cytokines (which presents autoimmunity safety concerns), heterologous adjuvants (safety, regulatory and cost concerns) while preserving multiple use capacity of the vector (limited by flagellin or alphaviral replicons) is solved by this invention. As well, this approach solves the prior inoperability of DNA only vaccination, since the prior art teaches that DNA vaccination in primates and humans is efficacious only when combined with heterologous vector boosting (e.g. adenoviral, protein or inactivated vaccine), or inclusion of potent secondary adjuvants (e.g. IL12, IL15), or viral proteins (alphavirus). An investigator skilled in the art will see that the present invention now incorporates these additional functionalities into the vaccine backbone. As well, the ability to include multiple RNA elements in a single vector allows the unprecedented unexpected ability to now incorporate multiple functionalities into a vaccine. As well, despite extensive prior art in optimizing elements of the plasmid to improve expression, incorporation of an RNA element to accomplish this has not been contemplated in the art.

A number of different types of RNA elements may be included in DNA vaccine plasmids, to effect a variety of biological responses. A number of RNA functionalities and applications are disclosed below. It is not the intent to limit the application of RNA elements to these specific examples, rather these examples are discussed to demonstrate the general utility of the invention.

shRNAs

Targeted knockdown of gene expression allows customization of the target cell proteome. This can be used to induce $T_H1$ or $T_H2$ immunostimulatory cytokine or chemokine production, interferon production, enhance proteosomal processing, alter necrotic or apoptotic responses, induce plasmid DNA nuclear localization, enhance expression of plasmid, or alter expression of MHCI or MHCII determinants, or other cell surface receptors such as Toll-like receptors. For example, signaling from TLRs may be enhanced by shRNA knockdown of interferon regulatory factor 4 (IRF-4) which negatively regulates signaling by TLRs that require the adaptor protein MyD88. The TLR-signaling pathways are negatively regulated by TLR-inducible molecules—such as IRAK-M (IL-1-receptor (IL-1R)-associated kinase M), SOCS1 (suppressor of cytokine signaling 1), MyD88s (MyD88 short), SIGIRR (single immunoglobulin IL-1R-related molecule) and ST2. Other negative regulators of TLRs are, P13K, TRIAD3A, Tollip, A20 DAP12, and RP105 (TLR4 inhibitor; Reviewed in Liew F Y, Xu D, Brint E K, O'Neill L A J. 2005 *Nature Rev. Immun.* 5: 446-458). Knockdown may enhance the magnitude of cytokine response to TLR ligands. Cot may be a target, since it seems to act as a negative regulator of IL-12-mediated $T_H1$ responses. The presentation of peptides on MHCI may be enhanced by activation of the proteosome.

The small size of a shRNA producing element (e.g. 300 bp for the murine U6 promoter) allows multiple cassettes to be incorporated into a single plasmid, allowing rationale manipulation of the target cell.

Example applications of this approach to induce targeted apoptosis, or plasmid nuclear localization are discussed below.

Plasmid Expression Enhancing shRNAs shRNAs that alter the proteome to improve antigen expression through improved plasmid stability, nuclear transport, mRNA transcription, mRNA stability, mRNA processing and mRNA nuclear export, and/or translation of antigens are contemplated. For example, plasmid entry into the nucleus is a limiting factor in obtaining antigen expression. Increasing nuclear localization of a plasmid through inclusion of NFκB binding sites or a SV40 enhancer improves antigen expression in vitro and in vivo; this is presumed due to binding of NFκB which then piggybacks the plasmid to the nucleus (Dean et al, Supra, 1999). However, NFκB is generally cytoplasmically localized, and transfer to the nucleus is both limited, tissue-specific, and dependent on stimulatory signals. This limits the utility of NFκB nuclear targeting.

Plasmid encoding shRNAs that target the short half life repressors of NFκB nuclear localization (e.g. Iκβ alpha, beta and epsilon) will cause nuclear localization of NFκB, increasing plasmid nuclear retention. As well, expression will be enhanced from NFκB responsive promoters such as the CMV and SV40-CMV promoters. This strategy is anticipated to improve expression levels, and would have applications in improving DNA vaccines, as well as plasmid utilized for therapy (e.g. growth hormone releasing factor plasmid therapeutics)

Apoptosis Inducing shRNAs

Immune responses to DNA vaccines are enhanced by apoptosis. This has been accomplished by coadministering Fas or mutated caspases 2 or 3, which enhances CTL responses to IM administered DNA vaccines. Coadministered caspases also improves immune responses to influenza HA DNA vaccine by Gene Gun (Sasaki et al Supra, 2001). The optimal condition may be to selectively kill muscle or keratinocyte cells (but not immune cells) for a source of antigen for dendritic or langerhans cells (Reviewed in Leitner and Restifo, Supra, 2003). This is not possible utilizing constitutive cell death promoting agents. Inhibition of apoptosis can also improve immune responses, wherein coadministering Bcl-XL strongly enhanced T cell response after Gene Gun administration. This may reflect a benefit of prolonging dendritic cell. Killing transfected cells has an extra safety feature due to reducing the chances of insertional mutagenesis.

Dendritic cells (especially immature dendritic cells that are less resistant to cell death inducers than mature cells) may be differentially sensitive to targeted reduction of different anti-apoptosis genes. A non-limiting list of antiapoptosis genes that can be knocked down are BCL-2, BCL-XL, FLIP, XIAP as well as Mcl-1, Bcl-W, Bfl-1, c-IAP1, C-IAP2, Survivin, Livin and ARC). Immune responses can be enhanced by targeted apoptosis of non immune cells at the site of injection. For IM injection, this would be skeletal muscle cells, for subdermal immunization this would be keratinocyte cells. Interestingly, skeletal muscle cells appear resistant to intrinsic pathway apoptosis; this is correlated with reduced levels of ApaF1 (Burgess D H, Svensson M, Dandrea T, Gronlung K, Hammarquist F, Orrenius S, Cotgreave I A. 1999 *Cell Death Differ* 6: 256-261) and increased levels of XIAP (Reviewed in Primeau A J, Adhihetty P J, Hood D A. 2002 *Can. J. Appl Physiol.* 27: 349-395). Skeletal muscle express high levels of FLIP and ARC (apoptosis repressor with a CARD). ARC suppresses both extrinsic and intrinsic apoptosis pathways; depletion of ARC by siRNA treatment causes spontaneous apoptosis of muscle cells (Nam Y J, Mani K, Ashton A W, Peng C F, Krishnamurthy B, Hayakawa Y, Lee P, Korsmeyer S J, Kitsis R N. 2004 *Molec. Cell.* 15: 901-912). This suggests that DNA vaccines carrying a shRNA to knockdown ARC may target skeletal, but not dendritic cells for cell death. Similarly, FLIP levels are high in keratinocyte (and moderate levels of XIAP and Livin) cells; XIAP and Liven levels are reduced after apoptotic stimulation (Bowen A R, Hanks A N, Allen S M, Alexander A, Diedrich M J, Grossman D. 2003 *J Invest Dermatol* 120: 48-55). Targeting one or more of these genes may allow selective apoptosis of keratinocytes, without killing resident langerhans cells. Critically, apoptosis may be delayed and require apoptosis inducing inflammatory signals such as TNFα to be produced after immunization. This would afford high level antigen expression prior to cell death, overcoming a limitation of immediate apoptosis such as is observed with alphaviral vectors.

The optimal combinatorial code of shRNAs for selective apoptosis and immunostimulatory activity can be determined in vitro (using primary skeletal muscle, keratinocyte, langerhans or dendritic cells and monitoring cell death, interferon or cytokine or chemokine secretion, gene expression by RTPCR, and or protein expression using antibodies by standard methodologies) or in vivo (after gene immunization, by monitoring $T_H1$ or $T_H2$ responses, antibody production, cellular immune responses and or protective immunity).

Gene specific shRNAs are integrated in the vaccine vector. The amount of shRNA produced by only one or a few copies of the vector introduced into a cell during vaccination should be sufficient for target gene knockdown, since the art teaches that a single copy of a shRNA producing gene (as with retroviral vector produced integrated cell lines producing shRNAs) can be sufficient for target gene silencing. For gene targeting shRNAs, the vector may not need to be retrofitted as the vehicle is scaled from mice to ferrets to humans, if conserved sequences in target genes are utilized. For example, cross reactive silencing RNA constructs have been developed for a number of target genes for example Bcl-2. Alternatively the shRNAs can be species specific. For agricultural applications, preferable the RNA elements are rationally designed for the target organism, and validated in vitro using target tissue primary cells prior to animal studies.

dsRNA

Significantly, for vaccine application, dsRNA is synergistic with CpG DNA to enhance immune responses (Whitmore M M, DeVeer M J, Edling A, Oates R K, Simons B, Linder D, Williams B R G. 2004 *Cancer Research* 64: 5850-5860). This is probably through interactions and collaboration between the TLR3 (dsRNA reactive; reviewed in Matsumoto M, Funami K, Oshiumi U, Seya T. 2004 *Microbiol Immunol* 48: 147-154) and TLR9 (CpG reactive) (Mukhopadhyay S, Herre J, Brown G D, Gordon S. 2004 *Immunol* 112:521-530) pathways. TLR3 and TLR4 act in synergy with TLR7 TLR8 and TLR9 agonists to induce $T_H1$ responses in DC; this may be a combinatorial code for DC stimulation (Napolitani G, Rinaldi A, Bertoni F, Sallusto F, Lanzavecchia A. 2005 *Nat. Immunol.* 6: 749-750). Creation of a plasmid DNA vaccine that incorporates the ability to make dsRNA (without requiring replicon genes) with CpG optimization is expected to be more potent than alphaviral vectors (which are not gene expression optimized). The incorporation of further modalities, such as targeting shRNAs, allows the dsRNA response to be customized; for example, the balance between necrosis and apoptosis (reviewed in Kalai M, Loo G V, Berghe T V, Meeus A, Burm W, Saelens X, Vandenabeele P. 2002 *Cell Death Differ* 9: 981-994) can be rationally designed, to maximize immune responses.

Apoptosis Inducing dsRNA

Cytoplasmic dsRNA activates PKR, RIG1 and MDA-5, which induces interferon production, inhibits protein synthesis thus reducing antigen production eventually leading to apoptotic cell death (reviewed in Wang and Carmichael, Supra, 2004). Cell death releases the dsRNA, which can then be taken up by cells, and further induce innate immune response by binding and stimulating endosomally localized TLR-3 (Reviewed in Schroder and Bowie, Supra, 2005). This type of dsRNA stimulation occurs with alphavirus replicon vaccines. Alphavirus replicon (suicide) vaccines induce enhanced immune responses with 100-1000 fold less antigen compared to standard DNA vaccines (by IM injection). These vectors induce apoptosis, presumed through formation of dsRNA which activates antiviral pathways and eventually leads to apoptotic cell death (Leitner et al. Supra, 2000). Cell death is required for improved vaccine efficacy and is mediated by cytoplasmic replicon dsRNA, which the induces innate immunity through the TLR-3 dsRNA recognition pathway. Codelivery of anti-apoptotic gene (Bcl-XL) reduced protection, despite increasing antigen production (Leitner et al. Supra, 2003, 2004; Matsumoto et al. Supra 2005). However, a delivery dependent balance between cell death signals and optimal production of antigen is required, since suicide DNA vaccines are not effective with Gene Gun delivery (which targets dendritic cells) unless an anti-apoptosis gene is included (Kim et al. Supra 2004).

Toll Like Receptor Agonists

Unmethylated CpG is present in the vector backbone of microbial produced plasmids and augmentation (CpG enriched plasmids) can be used to stimulate $T_H1$ responsive innate immune signals through TLR-9. Unfortunately, these effects are observed only with high dosages, and CpG effects are minimal with advanced delivery methods which use economically low amounts of antigen (e.g. gene gun) as reflected by a TH2 biased response. As well, the overall poor immunological response to DNA vaccines in humans has been attributed, in part, to significantly reduced expression of TLR-9 in humans compared to mice.

Proteins (e.g. flagellin) and RNA TLR agonists potentially would more effectively induce innate immune responses at low dose, since the signal from these elements is "amplified" from the vector (rather than a fixed vector component such as CpG). Ideally, for inclusion of an innate immunity inducer in a DNA vaccine vector backbone there should be no associated adaptive immune response which would limit repeat usage and generate variable results in a population due to attenuated responses in individuals with prior exposure (preexisting immunity). Vectors such as alphaviral replicons (which produce dsRNA adjuvant) or flagellin producing vectors contain one or more proteins that can induce adaptive immunity to vector components.

Immunostimulatory RNA

U-rich or U/G rich ssRNA TLR7/8 agonists have been identified that induce interferon responses (Heil et al, Supra, 2004; Diebold et al, Supra, 2004; Barchet et al, Supra, 2005) as well as a sequence specific siRNA that induces interferon production from human and mice plasmacytoid dendritic cells through TLR-7 (Hornung et al. Supra, 2005). A novel class of immunostimulatory nucleic acid, single stranded CpG RNA which does not require TLR-3, 7, 8 or 9 has been identified (Sugiyama et al, Supra). An RNA apatamer that activates RNA activated protein kinase PKR has been identified (Zheng X, Bevilacqua PC. 2004 *RNA* 10: 1934-1945). These studies utilized exogenously applied ssRNA and siRNA.

RNAs that induce innate immune responses may be evaluated in combination with apoptosis inducing elements (which would release the RNA for endosomal uptake necessary for activation of TLR 3, 7 or 8; reviewed in Crozat K, Beutler B. 2004 *Proc. Natl. Acad. Sci.* 101: 18: 6835-6836). However, differences in TLR expression, and immunology, between mouse and humans (Mestas J. Hughes C C W. 2004 *J. Immunol.* 172: 2731-2738) need to be considered in the design and testing of TLR3, 7/8 or 9 stimulating DNA vaccines. TLRs are differentially expressed in human cells compared to mice; in humans, TLR-3 is expressed strongly in splenic CD11c(+) immature dendritic cells, is downregulated upon maturation, and is not induced by LPS. dsRNA induces these cells to produce interferon α and IL-12. In mice TLR-3 is also expressed in macrophages and expression is induced by LPS stimulation. It is unknown what impact the differences in receptor expression patterns, responsiveness, and immunology between mice and humans (reviewed in Mestas and Hughes, Supra, 2004) will have on vaccine performance in humans. This can be overcome by the RNA elements of the invention, by stimulation of constitutively expressed cytoplasmic RNA response elements (such as RIG1 or Mda5) or activation of downstream signals in the TLR pathways, to avoid TLR species specificity.

While dsRNA is not inherently target specific (like CpG which is present in mammalian genomic DNA) poly I:C induces different Th2 type effects than poly A:U in vivo (Wang L, Smith D, Bot S, Dellamary L, Bloom A, Bot A. 2002 *J Clinical Invest* 110: 1175-1184). This suggests that TH1 versus TH2 bias can be selected by screening various dsRNA expression elements, to customize the immune response as necessary. dsRNA (polyI:C) has been used as an adjuvant in numerous clinical trials and is considered safe for human use (for example, see Giantonio B J, Hochster H, Blum R, Wiernik P H, Hudes G R, Kirkwood J, Trump D, Oken M M. 2001 *Invest. New Drugs* 19: 89-92). dsRNA accounts for the inflammatory responses to viral infection (e.g., see Zare F, Bokarwea M, Nenonen M, Bergstrom T, Alexopoulou L, Flavell R A, Tarkowski A. 2004 *J Immunol* 172: 5656-5663) and dsRNA and dsDNA binding proteins are prominent autoantigens (Satoh M, Shaheen V M, Kao P N, Okano T, Shaw M, Yoshida H, Richards H B, Reeves W H. 1999 *J Biol Chem* 274: 34598-34604) which can be activated by any dsDNA or dsRNA introduced into the cytoplasm (Suzuki K, Mori A, Ishii K J, Saito J, Singer D S, Klinman D M, Krause P R, Kohn L D. 1999 *Proc Natl Acad Sci* 96: 2285). Plasmid DNA and dsRNA producing viral vectors have not induced clinically relevant levels of autoantibodies in numerous studies. The amount of cells transfected by plasmids are small, and the expected dsRNA production much lower than that presented naturally during viral infection or with viral vectors. It is therefore expected by us that dsRNA producing plasmids would be dramatically safer than other vectors.

RNA Aptamers

A number of microbial specific motifs have been identified that activate innate immunity through Toll like receptor (TLR) binding, for example, Tri-acyl lipopeptides (TLR-1/TLR2) peptidoglycan (TLR-2), dsRNA (TLR3), bacterial HSP60 or Lipopolysaccharide (LPS; TLR-4), flagellin (TLR5), Di-acyl lipopeptide (TLR-6) ssRNA (TLR-7, TLR-80 unmethylated CpG DNA (TLR-9). Other pathogen pattern recognizing receptors include the NBS-LRR (Nod) family of intracellular recognition units (e.g. Nod1, Nod2 which detect intracellular bacteria through specific peptidoglycan motifs) and the C type lectins (e.g. dectin-1, DC-SIGN). In addition, some innate immune system recognition processes and molecules also recognize damaged cells and tissues such as collectins (e.g. mannose-binding protein, surfactant proteins A and D, C1q). As well, activators of other signaling pathways can be utilized; for example, TLRs and IL-1 receptor (IL-1R) activate similar signaling pathway. Of these non-RNA activators, RNA aptamers that bind and activate the receptors could be selected utilizing methods known in the art. These aptamers could then be incorporated into the DNA vaccine backbone as potent immune stimulatory molecular adjuvants to further potentiate DNA vaccination. C-type lectin dectin-1 acts in synergy with Toll-like receptor 2 to induce tumor necrosis factor (TNF) and interleukin 12 (IL-12) production A combinatorial code of activators can be utilized to activate multiple receptors to additively or synergistically enhance immune responses.

As well, bifunctional aptamers (two binding sites) can be used for antigen targeting. For example, incorporation of an antigen binding site with a dendritic cell targeting site may be utilized to target antigen released by cell necrosis to APC.

DNA Targeting Preferred Embodiments

In one preferred embodiment to determine optimal antigen presentation, immunization is performed using a targeting pDNAVACCUltra vector. It is established in the art that fusion proteins that alter the intracellular localization of an antigen (e.g. from cytoplasmic to secreted) or otherwise target antigen presenting pathways alter the resulting immune response (reviewed in Gurunathan et al., Supra, 2000). Preferred molecules that can be used to alter intracellular trafficking or antigen presentation of fused proteins are know in the art. Several intracellular targeting sequences are described in Williams et al, Supra 2001 and are include herein by reference. Several antigen presentation pathway targeting molecules are described in Leifert et al, Supra, 2004 and Lemieux, Supra 2002 and are included herein by reference. Some of these are summarized in Table 3. Exemplary vectors of the invention, incorporating some targeting molecules, are shown in FIG. 5.

TABLE 3

Antigen Presentation Pathway Targeting molecules

| Mechanism | Example | Comments |
|---|---|---|
| Fusion proteins transport antigen within cell to target MHC1 or 2 pathway loading | Protein transduction domain (Tat peptide) | Reaches cell surface more rapidly |
| | CLIP (Class II-associated invariant chain peptide) | MHCII pathway loading |
| | Heat shock proteins (e.g. HSP70, HSP70 binding domain of HSP40, HSP related Calreticulin) | HSP proteins bind peptides and facilitate MHCI pathway loading. Autoimmunity issues due to cross species conservation. |
| | C3d (complement adjuvant) | Improved antibody titer |
| Fusion protein binds APC cell surface receptors | CTL4. | CTL4 Binds B7 receptor on APC and enhances antibody response |
| Fusion protein with costimulatory molecule | e.g. fusion with immunostimulatory chemokines MCP-3, GM-CSF, IL-2, IL-4 etc | |
| Other | Fc (immunoglobulin constant region) | Increases DC uptake, used to increase antigen cross presentation |
| Increases immunogenicity | Tetanus toxin fragment C IL-1b fragment | Immunogenic pathogen sequence |
| Translocation sequences transfer protein from cell to adjacent cell | e.g. Antennapedia, HIV tat, HSV VP22 | Moves fused proteins between cells, enhances intercellular spreading, MHCI presentation |
| Fusion proteins transport antigen within cell to Endoplasmic reticulum | C terminal KDEL, other sorting peptides such as PSRDRSRHDKIH, Adenovirus E3 leader | Directs to Endoplasmic reticulum |
| Cytosol default trafficking | No N terminal hydrophobic sequence | Often native protein |
| Fusion proteins transport antigen within cell to Lysosome | Multiple C terminal tags (e.g. DKQTLL, DEKKMP) | Localizes protein to lysosome |
| Fusion proteins transport antigen within cell to Endosome | Endosomal (e.g. LAMP1, LIMP-II) | antigen targeting |
| Fusion proteins transport antigen out of cell (secreted) | N terminal hydrophobic sequence (e.g. TPA leader) | Leader is removed and protein secreted |
| Fusion proteins transport antigen to cytoplasmic Membrane anchoring | C terminal hydrophobic domain or GPI anchor | Hydrophobic domain used to prevent secretion and anchor otherwise secreted proteins to membrane. |
| Fusion proteins increases proteolysis | Fuse to proteosomal substrates, destabilizing sequences (e.g. Cyclin B or beta catenin destabilizing sequences) fusion to Ubiquitin | Enhances entry into MHCI processing |
| | Fuse to tubulin | Transfers protein to centrosome, rich in proteosomes |

It is also well known in the art that the effects of intracellular targeting are antigen specific, and the optimal intracellular destination to create the desired immune response need to be determined empirically for each antigen.

Use of a targeting vector family to determine optimal combinations of targeting destinations is not anticipated or taught in the art. As well, existing vectors such as those of Williams et al, Supra, 2001 use TypeII restriction enzymes for cloning, and do not allow precise expression of target antigen, without addition of extraneous sequences. These extraneous sequences may have profound effects on expression and localization.

The pDNAVACCUltra vectors disclosed herein allow rapid determination of the optimal intercellular destination for an antigen. The vectors are designed to facilitate rapid simultaneous cloning of a gene into multiple vectors with identical backbones (FIG. 3), featuring various intracellular targeting destinations for the protein product. The example targeting destinations disclosed herein (FIG. 5), i) secreted, ii) secreted membrane anchored, iii) endosome, iv) cytoplasmic v) proteosome or vi) dendritic are not an exhaustive list, nor are the signals utilized for targeting. For example, a heat shock protein (HSP) domain could be substituted for the ubiquitin signal in pDNAVACCUltra4, to create a HSP tagged cloning vector. Alternatively different signals could be utilized than those outlined in FIG. 5, for example the tyrosinase signal sequence could be substituted for the TPA sequence. Inclusion and use of additional targeting sequences into the vector family can be envisioned by one of average skill in the art (see Table 3 for example targeting sequences) using the disclosed gene self assembly technology, or standard cloning methods.

Existing vectors such as those described in Williams et al, Supra 2001, and Bucht et al, Supra, 2001 are not optimally designed to determine immune responses to antigens targeted to various intracellular destinations, since these vectors use standard typeII restriction enzyme cloning sites. The art teaches that small sequence variations between vector backbone can alter expression levels (Hartikka et al, Supra, 1996); different expression levels have been shown to influence the resulting immune response (Zinckgraf and Silbart, Supra, 2003). As well small peptide additions to recombinant proteins from cloning sites or peptide tags can alter the protein subcellular localization, even when these sequences do not contain targeting tags (Ramanathan et al, Supra, 2001). In contrast, the vectors disclosed herein solve this problem, since they are a controlled set and do not contain additional heterologous sequences since type II restriction sites are not used in cloning.

The vectors disclosed herein allow creation of controlled plasmids incorporating any and all targeting molecules identified in the art, without requirement for additional sequences flanking the target antigen by way of type II enzyme cloning sites. This family of vectors has application to improve DNA immunization through determination of the optimal antigen presentation.

In another preferred embodiment for improving DNA vaccination, gene expression is increased by utilizing a pDNAVACCUltra vector. The pDNAVACCUltra vectors disclosed herein allow improved gene expression compared to vectors described in the art (FIG. 4). The vectors can be utilized to increase expression of a target gene, for the purpose of improving immune responses or improving protein expression (e.g. for therapeutic use).

DNA Immunization Preferred Embodiments

In yet another preferred embodiment for improving DNA vaccination, immune responses are improved utilizing combinations of targeting and or RNA element containing vectors. We disclose herein various applications of the pDNA-VACCUltra targeting vectors in vaccine development (RapidVACC; FIG. 8). Discussed below is the application of RapidVACC for evaluation of targeting plasmid combinations. Evaluation of various RNA elements (i.e. combinations promoting apoptosis, immunostimulation, etc) would utilize the same algorithm and approach.

One object of the invention is to optimize the DNA component in a prime boost regiment. Use of the pDNAVACCUltra vector with its superior expression, in combination with the optimal intracellular targeting of the target antigen, and/or RNA elements, as determined by immunization, may significantly improve the immune response compared to that obtainable with other vectors.

Another object of the invention is to enhance immune response to genetic vaccines through optimized DNA prime/DNA boost or DNA prime only (single shot) immunization. This is a long felt, long-existing and unsolved need, since combining DNA vaccination with heterologous vectors or proteins while effective, eliminates the advantages of DNA vaccination (i.e. cost, safety, reduced development time, reduced process development). RapidVACC is a vaccine development process that utilizes the intracellular targeting vectors (with or without RNA elements) of the invention to determine the optimal presentation of protective antigen(s) using targeting plasmid immunization methods disclosed herein combined with antigen identification methods, immunization methods (e.g. electroporation, ultrasound, microparticles etc), and immune response evaluation methods (e.g. T cell responses by interferon-gamma enzyme-linked immunospot (ELISPOT), antibody response by enzyme-linked immunosorbent assay (ELISA) and Western blot, protective responses by organism challenge in a relevant animal challenge model) known in the art.

The application of RapidVACC discussed herein is not intended to be limited to traditional plasmid based DNA vaccine vectors; the strategy and targeting tags disclosed herein could be applied to any non-viral or viral vector system, including, but not limited to, minicircle, midge, bacteriophage or single stranded DNA vectors, or alphavirus, poxvirus, adenovirus or adenovirus related viral vectors.

As well, the strategy could be applied to alternative DNA vaccine vectors modified as necessary to incorporate RNA elements and/or to allow intracellular targeting (e.g. VR1012, pCMVKm2, pCpG, pCOR, pVC0396, pcDNA3, pVAX, pCWH24-6, pMAX, alphaviral replicon vectors etc), or modified pDNAVACCUltra vectors. For example, one or more modules in the pDNAVACCUltra vectors could be altered and the vectors still utilized in RapidVACC optimization. Different promoters (e.g. SV40, RSV, RSV-CMV, CMV-chicken B actin CAG promoter etc) leaders (e.g. CMV intron 1, RNA export leaders, QB1 SP163 translational enhancer, woodchuck PRE) terminator (e.g. bovine growth hormone termination), prokaryotic origin of replication (e.g. other pMB1 or ColEI derived origins, CpG reduced origins, R6K origin, R plasmid origin, pKL1 origin; see Table 4 for example origins of replication, and vectors utilizing these replication origins), selectable markers (e.g. alternative antibiotic resistance marker such as zeomycin or alternative kanamycin resistance, tRNA, balanced lethal systems, repressor titration plasmid). As well, plasmids with additional elements, such as the Rev gene (to increase nuclear export of some viral RNA's), elements required for bicistronic expression [second transcription unit, internal ribosome initiation sequence (IRES)] immune enhancing CpG sequences, site specific recombination systems (e.g. multimer resolution systems, or minicircle recombinase sites) or active partition systems (e.g. parA and parB of plasmid RK2) could be utilized in RapidVACC optimization. The example vectors of FIG. 5 use ATG and TAA stop codons corresponding to the start and stop of the target antigen, or for C terminal extensions, a GGC linker codon. This is not meant to limit the use of the invention to express antigens precisely from the start and stop codons. Alternative address tags could be utilized that encode internal or new codons, such that the target antigen is linked to the targeting tags through new direct linkages, or through linker peptides. Linker peptides that could be used to link a antigen to targeting tags are well known in the art. As well, alternative typeIIS enzymes could be utilized for cloning. For example, AarI could be utilized rather than SapI. This would require changing the address tags from 3 to 4 bps.

TABLE 4

Replication origins

| Parent Origin | Regulation | High copy Derivation | Copy Number | Therapeutic plasmids |
|---|---|---|---|---|
| pMB1 | Antisense RNAI binds RNAII. Rop accessory protein stabilizes interaction | pUC origin (Rop deletion and second site mutation that alters RNAI/II interaction at 37 and 42, not 30 C.) | 50 at 37° C., 175 at 42° C. (log phase) | Multiple (pcDNA3, pVAX, VR1012, etc) |
| | | pUC origin with second site enhancer increases copy number 14-50% | Not determined | pDNAVACCultra |
| | | Rop deletion | 30 at 37° C. and 42° C. (log phase) | pCMVKm2 |
| | | G to T mutation (extends RNAI, attenuating repressor; not conditional) Plasmid is 65% total DNA | 1000 (phase not indicated) | Not described |
| ColEI | Same as pMB1 | pMM1, pMM7 (Rop deletion and second site mutation that alters RNAI/RNAII interaction at 37 and 42, not 30 C.). pMM7 is >50% total DNA in stationary phase | 2000 in stationary phase (pMM7) | pVC0396† |

TABLE 4-continued

Replication origins

| Parent Origin | Regulation | High copy Derivation | Copy Number | Therapeutic plasmids |
|---|---|---|---|---|
| R6K (ori α, ori β ori γ) | π rep protein binds iteron, copy number dependent activation (low) or repression (high) | Host strain pir-116 mutant (π rep protein copy-up mutation in oligomerization domain removed from plasmid and provided in trans from chromosome) | 200 250 | pCpG, pBoost pCOR |
| R1 | RepA initiator protein binds non repeated target. Antisense CopA repressor binds RepA leader (CopT). Auxiliary CopB protein represses RepA expression. | Temperature inducible copy number using dual origin mutant (plasmid is 75% total DNA) RepA controlled by temperature inducible lambda $P_R$ promoter and temperature sensitive lambda repressor controlled. (Plasmid is 50% total DNA) | 2000 (mutant) 1000 ($P_R$ controlled) | pCWH24-6 |
| pKL1 | Rep A initiator protein represses repA transcription as hexamer | Rep A initiator protein overexpression on separate plasmid or on chromosome | >2500 | Not described |

†pVC0396 is an optimized vector backbone, for insertion of eukaryotic expression cassettes As well, the application of targeting vectors is not limited to vaccination of humans, it can be applied to animal, avian or fish vaccine development as well.

The art teaches that the optimal combination of plasmids for optimal immune protection will be antigen and delivery method specific, and will need to be determined for each antigen. A rational method to determine the optimal presentation is not taught in the art.

The art further teaches that interpretation of existing mixed plasmid immunization results is uncertain, since the variations between vector backbone used in these examples can alter expression levels (Hartikka et al, Supra, 1996), the immune response (Zinckgraf and Silbart, Supra 2003) and subcellular localization (Ramanathan et al, Supra, 2001).

Creation of vectors designed to facilitate intracellular targeting of antigens is taught by Williams et al, Supra, 2001. These vectors were not utilized, or contemplated for use, for prime boost optimization or mixed presentation immunization as proposed herein. As well, the vectors contain variations between vector backbone, and therefore cannot be used for rigorous determination of antigen presentation.

In summary, use of a targeting vector family to determine optimal combinations of targeting destinations is not anticipated or taught in the art. Applications of this novel immunization optimization strategies are outlined below.
Determination of Novel DNA Prime/DNA Boost Vaccine Combinations:

The improved immune response with heterologous vector boosting may be mimicked by priming with a DNA vaccine with one targeting destination, and boosting with another.

The optimal DNA vaccine prime boost combination could be determined experimentally by one skilled in the art. For example, using the pDNAVACCUltra vector family of the invention, with 5 different targeting destinations, all possible combinations of a single DNA prime and a single DNA boost could be tested with 25 groups (i.e. secreted antigen, could be boosted with secreted, secreted membrane anchored, cytoplasmic, proteomic, or endosomal targeted antigen and so on).

In cases where a small animal model of infection are available, one skilled in the art could rapidly determine the optimal vaccine combination, since only 25 test groups would need to be evaluated in the initial screen.

One possible approach is outlined in FIG. 8, and utilizes the vectors of the invention to determine the optimal RNA elements (DNA backbone) and antigen presentation in a prime boost format. The optimal combination may utilize the same or different targeting destinations in the prime and boost, to optimize the immune response.

It is not intended to limit the scope of the application to the targeting destinations shown in FIG. 5; one skilled in the art could either increase or substitute targeting destinations with other targeting molecules. Example targeting molecules are listed in Table 3.

The efficacy of the vaccine for can be further improved, or tailored for systemic or mucosal immunity, cellular versus humoral response, cancer, allergy or tolerance applications, by utility of RNA elements that influence the nature and magnitude of response, such as altering $T_H1$ versus $T_H2$ bias through control of cytokine or chemokine induction, (e.g. $T_H1$ promoting IL12, IL18, $T_H2$ promoting IL4). The necessary combination of elements will need to be optimized for the species, and specific cell types targeted by the delivery method (e.g. electroporation versus gene gun). Initial in vitro evaluation by transfection with plasmid DNA of primary cells from the target tissue can be used as a prescreen of RNA elements with desired functionality to limit the number of plasmids utilized in the primary RapidVACC vector backbone screen (FIG. 8).

Preferably, the optimal DNA vaccine prime boost combination may allow elimination of heterologous vector boosting. This would significantly enhance the rapid deployment utility of DNA vaccines since development times for DNA vaccines are significantly shorter than those for protein or viral vector systems. This could involve utilizing different delivery systems in the prime and the boost, as taught by Buchan et al, Supra, 2005 or different injection sites, as taught by Pavlakis et al, Supra, 2004.
DNA Protein Immunization Enhanced immune responses have been reported when plasmid DNA and purified protein (corresponding to the protein encoded in the plasmid) (Dalemans et al, Supra, 2003, Carrera et al, Supra, 2004 and Imoto and Konishi, Supra, 2005) or inactivated virus (Rangarajan et al, Supra 2004) are mixed coinjected. We speculate that immunization with purified protein, inactivated virus or cell, or cell extracts, in combination with antigen encoded in one or more targeting plasmids of the invention, may further enhance responses.

Mixed Presentation Immunization

One object of the invention is to further enhance immune responses using "mixed presentation immunization" wherein an immune response to a target antigen is enhanced by immunization with a plasmid cocktail, which combines 2 or more plasmids each targeting the antigen to different intracellular destinations. This novel combination of two or more DNA vaccine plasmids containing the same antigen with different cellular destinations may dramatically improve the nature of the immune response. Testing of plasmid cocktails, combining 2 or more combinations of the intracellular targeting destinations, is feasible utilizing the vectors of the invention.

The combination of presentation modes providing optimal immune response may be antigen specific. The vectors of the invention facilitate a rationally designed rapid deployment vaccine algorithm, wherein the optimal novel presentation combinations that provide superior immune response, compared to individual targeting destinations, for each chosen target antigen, is determined by sequential rounds of immunization with specified vector combinations. One possible approach is outlined in FIG. 8.

The vaccine development process involves identifying a target protective antigen using targeting plasmid immunization using antigens known in the art. The effectiveness of the antigen in a vaccine is then enhanced by determining the optimal combination of targeting destinations by individual or mixed presentation immunization after vaccination with a variety of from 2-200 combinations of targeting plasmids, most preferably from 5 to 36 combinations of targeting plasmids. For example the disclosed pDNAVACCUltra vector system with 5 different targeting destinations, there are 5 combinations of a single destination plasmids, 10 combinations of two destination plasmids, 10 combinations of three destination plasmids, 5 combinations of 4 destination plasmids and 1 combination of five destination plasmids (36 combinations total). Inclusion of additional targeting destinations into the vector family would increase the number of combinations, while elimination of destinations would decrease the number of combinations. Once the optimal combination is determined, the optimal combination in a single or multiple boost vaccination regimen is determined using a similar algorithm approach for the prime and boost steps. It is not the intent to limit the options for evaluation of the different plasmid combinations since there are multiple methods that can be used by one of average skill in the art. For example, during vaccine optimization, it is anticipated that some target destinations or destination combinations may be eliminated after initial evaluation, on an antigen to antigen specific basis, to reduce the complexity of the multiple boost algorithms. If the number of priming plasmids is reduced to 3 after the initial screen results, there are only 7 possible combinations of 1-3 plasmids for testing. Alternatively, the top responding combinations from the initial screen may be selected for subsequent multiple boost optimization. The same rational approach is applied to determining the optimal vector backbone (RNA element evaluation).

In cases where a small animal model of infection are available, one skilled in the art could rapidly determine the optimal vaccine combination, since only 5 plasmid constructs are made (using high throughput cloning) and 36 test groups evaluated in the initial screen.

Different combinations of targeting plasmids in the prime and the boost may be identified as optimal. The art teaches that superior immunological protection is obtained by heterologous vector boosting after DNA priming, compared to the heterologous vector or DNA vaccine alone. This may be due to different antigen presentation, the benefits of which may also be obtained with mixed presentation immunization.

It is not intended to limit the scope of the application to the five targeting vectors disclosed herein; one skilled in the art could either increase or substitute targeting destinations with other targeting molecules. Example targeting molecules are listed in Table 3.

One object of the invention is to optimize the DNA prime utilized in a prime boost regiment. Use of the pDNAVACCUltra vector with superior expression, in combination with optimal intracellular targeting combinations of the target antigen, may significantly improve the immune response.

Another object of the invention is to eliminate the need for protein or other heterologous vector boosting to obtain sufficient immune response. This may involve utilizing the same or different combinations of targeting destinations in the prime and boost, to replace heterologous vector boosting. This would significantly enhances the utility, since development times for DNA vaccines are significantly shorter than those for protein or viral vector systems. This could involve utilizing different delivery systems in the prime and the boost, as taught by Buchan et al, Supra, 2005, or different injection sites, as taught by Pavlakis et al, Supra, 2004.

Rapid Deployment Vaccines (RapidVACC)

One object of the invention is to use the pDNAVACCUltra targeting gene family to develop DNA based rapid deployment vaccines for new pathogens (RapidVACC). Once genome sequences are available, the vectors of the invention facilitate a rationally designed rapid deployment vaccine algorithm.

In one embodiment, the optimal antigen presentation in the prime and boost that provide superior immune response for each chosen target antigen, and antigen combinations is determined by sequential rounds of immunization with specified vector combinations. In this mode, the same or different individual targeting plasmids are contemplated for use in the prime and boost.

In another embodiment, the optimal novel presentation combinations that provide superior immune response, compared to individual targeting destinations, for each chosen target antigen, and antigen combinations is determined by sequential rounds of immunization with specified vector combinations. In this mode, mixed mode immunization evaluation is contemplated.

The RapidVACC process involves identifying protective antigen(s) using targeting plasmid immunization methods disclosed herein combined with antigen identification methods known in the art.

Antigens to use in RapidVACC can be identified by methods well know in the art. For example, genomics, bioinformatics, transcriptional profiling or proteomics technologies exist that allow high throughput screening for protective epitopes. Bioinformatics can be utilized to identify putative vaccine candidate immunostimulant T cell epitopes in sequenced genomes. Transcriptional profiling screens (e.g. Microarray analysis) are utilized to identify vaccine targets by determining all proteins that are expressed intracellularly after infection. Production and screening of transcriptionally active PCR (TAP) products (Linear expression elements) is an extremely high throughput technology to generate DNA fragments that produce target proteins after transfection into cells or DNA immunization. This technology has application for in vitro assays (T cell assays) and in vivo (i.e. genetic immunization) high throughput proteomic screens (Sykes K F, Johnston S A. 1999 *Nat Biotechnol;* 17:355-359). The technology is well suited to identify candidate antigens (antigen potency) in whole genomes for further analysis (i.e. protection studies with DNA vaccine plasmids as disclosed herein).

Secreted and membrane associated proteins from intracellular pathogens can be used as a source of sufficient protective T-cell epitopes to create efficacious polyepitope DNA vaccines. This hypothesis is modeled after work in several organisms (e.g. *Mycobacterium tuberculosis, Legionella*, and *Listeria*) where multiple, individual membrane and secreted proteins have been demonstrated to contain partially protective epitopes, as well as a genome screen for protective responses against purified *Streptococcus* proteins (Wizemann T M, Heinrichs J H, Adamou J E, Erwin A L, Kunsch C, Choi G H, Barash S C, Rosen C A, Masure H R, Tuomanen E, Gayle A, Brewah Y A, Walsh W, Barren P, Lathigra R, Hanson M, Langermann S, Johnson S, Koenig S. 2001 *Infect Immun;* 69(3):1593-1598).

Of genes identified in sequenced genomes, the subset that are secreted or membrane isolated can be determined using bioinformatics. Bioinformatics programs such as signal-P have been utilized in bacterial genome screens to identify secreted proteins. This subset will be approximately 15-25% of all genes (if 20%, 50-300 genes). This is a manageable amount to test for protective epitopes. For example, high throughput cloning and expression and purification of the putative secreted proteins, with in vitro and in vivo assays for identification of candidates, has been demonstrated on a genome scale for *Neisseria meningitidis*. This so called "reverse vaccinology" approach is a time and cost effective method for applying genome data to vaccine development (reviewed in Capecchi B, Serruto D, Adu-Bobie J, Rappuoli R, and Pizza M. 2004 *Curr Issues Mol. Biol.* 6:17-27). An alternative proteomics based protective epitope identification scheme, utilizing DNA vaccine plasmids rather than purified proteins, using high throughput cloning of exons into DNA vaccine vector, and screening for protective antigens by expression library immunization may be utilized. None of these approaches teaches to optimize antigen presentation during vaccine development, once protective antigens have been identified.

An example RapidVACC protective antigen optimization scheme, utilizing DNA vaccine plasmids, is utilized in FIG. 9. In this example, secreted proteins are selected for neutralization screening; this is not intended to limit the application of the technology to secreted antigens. In theory, effective single protein (FIG. 9) or polyprotein (not shown) vaccines, and the optimal antigen presentation combination, in the prime and boost, can be rapidly identified using this scheme.

The putative antigens could be tested for neutralization using expression library immunization (Barry M A, Lai W C, Johnston S A. 1995 *Nature;* 377:632-635) scheme in which the DNA vaccine immunogen mixes are low complexity and intracellular trafficking is rationally designed to dramatically increase sensitivity. Expression of MHCI or MHCII presentation targeted antigen using pDNAVACCultra high throughput antigen trafficking DNA vaccine plasmids may be more effective than purified protein immunization at detecting partially protective epitopes expected with this class of pathogen.

Screening for protective proteins using pDNAVACCUltra vectors would generate "gold standard" highly sensitive protective immune results in a single high throughput step. This approach therefore eliminates time consuming secondary screens to sort out non-protective T-cell reactive epitopes. This hybrid genomic/proteomic approach uses genomics and bioinformatics to reduce the total number of targets for the proteomic screen to a manageable number to use in a highly sensitive protection screen designed to detect partially protective epitopes.

The final vaccine formulation may eliminate the need for protein or other heterologous vector boosting to obtain sufficient immune response. This may involve utilizing the same or different combinations of targeting destinations in the prime and boost, to replace heterologous vector boosting. This would significantly enhances the utility, since development times for DNA vaccines are significantly shorter than those for protein or viral vector systems. This could involve utilizing different delivery systems in the prime and the boost, as taught by Buchan et al, Supra, 2005.

EXAMPLES

The method of the invention is further illustrated in the following examples. These are provided by way of illustration and are not intended in any way to limit the scope of the invention.

Example 1

Creation of pW2.0 pWizBang2.0

In order to facilitate the ordered, directional assembly of genes and vectors, we devised a new vector for a modular approach, in which each DNA fragment is assigned two unique, non-palindromic address tags. This method relies upon the ability of class IIS restriction enzymes to digest at a distance from the enzyme site. Blunt DNA fragments (synthetic dsDNA; PCR amplicons; or blunt restriction fragments) are cloned into a novel vector, PWiz-Bang2.0, and the class IIS enzyme AarI (a seven base cutter commercially available from Fermentas, or an AarI isoschizomer, is used to cleave the DNA, leaving a four base, 5'-overhang. The fragments are recovered and are ligated in a single reaction, producing the desired construct (FIG. 1). In theory, the use of unique, non-palindromic 4-base termini permits up to 121 fragments to be joined unambiguously together.

Example 2

Creation of pDNAVACC Vectors Using Gene Self Assembly

DNA vaccine plasmids were created by single step assembly of six precloned modules using Gene Self Assembly technology. Each modular element was assigned a position in a circular array, providing a choice of promoter, 5-leader/splice-site, target gene or high throughput cloning site, terminators, and prokaryotic ori/selection/sites. Individual modules were assigned a position and directionality by means of 4 bp unique, non-palindromic address tags and cloned into pWiz-Bang2.0. Additional features, such as prokaryotic terminators, were incorporated seamlessly into the modules through 5' extensions on the PCR primers.

The (Gene Self Assembly) modules consisted of products representing:
  Bacterial replication origin: High copy number pUC derived replication origin;
  Prokaryotic selectable marker gene (kanamycin; kanR);
  Eukaryotic enhancer-promoter (CMV or VL30 NVL3; Adams S E, Rathjen P D, Stanway C A et al. 1988 *Mol Cell Biol.* 8: 2989-2998)

Leader: Synthetic eukaryotic untranslated leader-intron-translational initiation sequence (Kozak sequence) cassette derived from rabbit β-globin leader and intron Targeting cassette: High throughput seamless cloning site targeting gene leader cassette (FIG. 5) or control modules containing native EGFP or TPA secreted SEAP.

Terminator: Synthetic eukaryotic transcriptional terminator based on rabbit β-globin.

PCR to generate fragments was performed using Pfu DNA polymerase (to avoid adding extra bases onto the ends of blunt fragments). Fragments were cloned into the SmaI site of pWiz-Bang2.0, and inserts were sequenced to verify correct termini prior to releasing the fragments with AarI, joining using T4 DNA ligase, and transforming DH5α competent cells. Representative clones were sequence verified.

The fragments were recovered and ligated in a single reaction, producing the desired construct at high frequency (>90%). 15/16 isolates from six independent reactions containing six ligated fragments (permutations of the modules described above with fragments from 70 bp to 2 kb) yielded the desired constructs demonstrating the 4-base pendant termini ligated with high fidelity.

New targeting vectors can be rapidly created by replacement of the targeting cassette with new cassettes encoding other targeting peptides (see Table 3 for examples).

Example 3

Validation of pDNAVACC Elements pDNAVACC5-EGFP elements were replaced with the corresponding regions from gWiz-GFP (Gene Therapy Systems, San Diego Calif., USA), a derivative of Vical VR1012 vector (Hartikka et al, Supra, 1996), to verify functionality of each pDNAVACC region. Module and fragment swaps were performed using standard PCR and restriction enzyme cloning methodologies, and confirmed by restriction digestion.
  i) Enhancer upstream flanking region: replaced XhoI (kanR internal site)-SpeI (CMV enhancer internal site) fragment with XhoI-SpeI fragment
  ii) Promoter-Leader-Intron-Kozak: replaced SpeI (CMV enhancer internal site)-NcoI (EGFP start codon) fragment with SpeI-SalI (filled; regenerates SalI site, see below).
    a. The EGFP within this clone was replaced with kozak-GFP from g-Wiz-GFP by replacement of the SalI-BglII fragment with SalI-BamHI fragment from gWiz-GFP
  iii) Terminator: replaced BglII-StuI fragment with BamHI-XmnI fragment
  iv) Origin-Kan cassette: Replaced StuI-XhoI (internal kanR site) fragment with XmnI-XhoI.

The expression level of EGFP or GFP was approximately equivalent for each parental and swap plasmid validating the design and demonstrating elimination of extraneous sequences did not compromise expression.

Example 4

Origin Orientation and Composition Dramatically Affects Copy Number

The minimal size of the pUC origin, that gave high copy plasmid production, was determined by deletion analysis. Plasmid Copy Number was determined by quantification of plasmid obtained from Qiagen miniplasmid kit preparations. Derivatives containing the core origin (FIG. 2: RNAII promoter through RNaseH cleavage site) were created by Gene Self Assembly and found to have dramatically reduced copy number. Removal of the trpA terminator (NotI/StuI digested, klenow filled and religated) did not alter copy number. Addition of either flanking region to the core origin increased copy number, but each had reduced copy number relative to the entire 1 kb origin.

The yield of plasmid is unexpectedly and dramatically altered by orientation of the prokaryotic origin and kanR gene relative to each other in the same pDNAVACC vector backbone (Table 1). The orientation of the kanR and Origin genes were reversed by ligation of the two products of digestion with flanking unique restriction sites (StuI/FspI for origin reversal, FspI/PmeI for KanR reversal).

The optimal orientation determined herein has divergent transcription of the origin and kanR gene, as well as inclusion of dual transcriptional terminators after the kanR gene.

Example 5 pDNAVACCUltra

Numerous copy up versions of the ColEI and pMB1 origins have been isolated, as either spontaneous or selected mutations (in screens for temperature sensitive resistance to extreme levels of antibiotic. The lesions associated with several high-copy number mutants are clustered in the RNAI promoter but do not affect RNAI transcription. Rather, they appear to affect the secondary structure of the RNAII replication primer that may either affect RNAI/RNAII interactions or the ability of RNAI to inhibit replication initiation (Lin-Chao S, Chen W, Wong T. 1992 *Mol Micro* 6:3385-3393; Fitzwater T, Zhang X, Elble R, Polisky B. 1988 *EMBO J* 7:3289-3297). Commonly utilized copy up derivatives of the pMB1 origin (e.g. pUC19) or ColE1 origin (PMM1, pMM7) delete the accessory ROP (rom) protein and have an additional alteration that destabilizes the RNAI/RNAII interaction. For temperature sensitive origins (e.g. pUC, pMM1, pMM7), shifting of the culture from 30 to 42° C. leads to 30-40 fold increase in plasmid copy number to 300 copies per cell. Perhaps due to the additional regulation by uncharged tRNA binding under amino acid starvation conditions, many of these derivatives are maximally induced by both temperature and entry into stationary phase (pMM1, pMM7, pUC). pMM7 is reported to have 119 copies per cell in early log, and undergo a further 21 fold increase in copy number by late stationary phase. In stationary phase, pMM7 plasmid DNA accounts for >50% of total cell DNA.

A series of chimeric origins were constructed, by site directed mutagenesis, in the pDNAVACC-EGFP (in the optimized kanR gene-origin orientation determined in Example 4 above) vector backbone. These origins were in the pMB1 origin backbone incorporating either 1) pUC origin mutation 2) pMM1 origin mutation 3) pMM1+pUC origin mutations and 4) pMM1, pMM7 and pUC origin mutations. The mutagenized plasmids were sequence verified, and copy number determined in shake flask culture in mid-log and stationary phase. The results demonstrated that 1) pMM1 alone had dramatically lower expression than the other three combinations 2) pMM1+pUC had similar levels to pUC and the triple combination in log phase, but unexpectedly has enhanced productivity in stationary phase.

The pDNAVACCultra plasmid has the optimized kanR gene-origin orientation (FIG. 2), with either the pUC or the pMM1+pUC RNAII mutation. This increases plasmid copy number 2 fold versus pDNAVACC (pUC origin and non optimal kanR gene-origin orientation) (Table 1).

Example 6

Creation and Evaluation of Chimeric Promoters

Unique restriction sites, upstream of the enhancer-promoter, are incorporated into the pDNAVACC vectors to allow chimeric enhancer construction. Derivative pDNAVACC and pDNAVACCultra vectors, containing intracellularly targeted EGFP driven by either the CMV or VL30 promoter were constructed using Gene Self Assembly. Chimeric enhancers were created by PCR. The PCR primers were designed to contain flanking restriction sites (KpnI and AbaI).

The product was digested, cloned into KpnI/XbaI digested pDNAVACC-EGFP, and sequence verified.

Expression of EGFP in vitro was determined using fluorescent microscopy 24-72 hrs post transfection of fibroblast cell lines (either human HTam or mouse PA317) using either lipofectamine (Invitrogen, Carlsbad, Calif., USA), Superfect (Qiagen, Valencia, Calif., USA) or TROjene (Avanti Polar Lipids, Alabaster, Ala., USA).

Expression from CMV and VL30 promoters in fibroblast cells is differentially augmented by fusion of heterologous SV40 enhancer repeat (containing binding sites for NFκB and other transcription factors) or concatamer of 5 NFκB binding sites (Table 2). Overall expression is higher with the pDNAVACCultra configuration with either promoter. Generally, inclusion of the SV40 enhancer increased expression, although no increase in in vitro expression was observed with the CMV promoter in the ultra configuration.

Transfection with pDNAVACCUltraCMV-EGFP or pDNAVACCUltraSV40-CMV-EGFP constructs results in the highest level of expression with close to 100% transfection. Expression is improved relative to the control gWIZ-EGFP plasmid, efficiency.

Example 7

In vivo Expression

Expression of SEAP in vivo was determined in mice. The study used 4 mice per group with one intramuscular dose of plasmid (5 ug/20 ul) delivered to one CT (tibialis) muscle by electroporation. Bleeds were done at day 4.

pDNAVACCUltraCMV-SEAP and pDNAVACCUltraSV40-CMV-SEAP constructs were made, and in vivo expression determined. The results (FIG. 4) demonstrate expression of pDNAVACCUltraCMV-SEAP is improved compared to gWIZ-SEAP. Incorporation of the SV40 enhancer dramatically augments in vivo expression with the 5 ug dose.

Example 8

Plasmid Stability

The stability of pDNAVACCUltraCMV-GFP and pDNAVACCUltraSV40-CMV-GFP plasmids was determined, relative to pDNAVACC plasmids containing the SV40-CMV, CMV, SV40-NVL3 and NVL3 (promoters. Plasmid stability was determined by serial growth of plasmid from glycerol stocks. Briefly, a saturated overnight in LB+ kanamycin from the glycerol stock was considered generation zero (G0), and two serial $10^{-5}$ dilutions were regrown to saturation (G20 and G40, respectively). No instability (% supercoiling, replication intermediates, dimerization) was detected over the 40 generations of the study. All plasmids were predominantly supercoiled, with very low levels of nicked plasmid or dimerization at all timepoints. Low levels of replication intermediates were detected with all the pDNAVACC plasmids, but not with the pDNAVACCultra plasmids.

Inclusion of the SV40 enhancer unexpectedly resulted in lower viability in glycerol stocks with the pDNAVACC plasmids; by contrast no viability loss was observed with SV40 containing pDNAVACCUltra plasmids. This demonstrates that glycerol stock viability is affected by the orientation of elements in a plasmid.

Example 9

Intracellular Targeting

High throughput seamless cloning site targeting gene leader cassette incorporating targeting signals (targeting cassettes; TPA, ubiquitin or LAMP peptide leaders and C terminal membrane anchoring tags, as necessary; see FIG. 5). were created, and incorporated into a family of pDNAVACCultra vectors using Gene Self Assembly technology.

| | |
|---|---|
| pDNAVACCultra1 | (secreted-endosome) |
| pDNAVACCultra2 | (secreted) |
| pDNAVACCultra3 | (secreted-membrane-anchored) |
| pDNAVACCultra4 | (proteasome) |
| pDNAVACCultra5 | (native) |
| pDNAVACCultra6 | (membrane-anchored) |
| pDNAVACCultra7 | (endosome) |
| pDNAVACCultra8 | (secreted-cross presentation) |

All cloning sites are designed for high throughput cloning applications (FIG. 3), and are compatible between multiple vectors, allowing several different intracellular targeted gene constructs to be made in one step. The vector family contains the CMV, or the chimeric SV40-CMV promoter (see below). These targeting sequences are example sequences, and can be substituted with other targeting sequences, that have similar or different targeting functions. For example, the murine G76A Ubiquitin derivative is described for proteosomal targeting. This residue reduces cleavage, leaving the fusion as a target for poly-ubiquitination. A destabilizing amino acid, alanine, is encoded immediately after the G76 residue (to ensure that cleaved products have an unstable N terminus as defined by the N-end rule, and are also targeted to the proteome (Delogu et al, Supra, 2000)). However, other species or ubiquitin derivatives can be substituted into the vector.

Example 10

High Throughput Cloning

An example high throughput application of the pDNAVACC vectors is outlined in FIG. 3. Genes are copied by amplification from clones or genomic DNA using primers incorporating SapI sites into termini to generate either 5' ATG and 3' TAA or 5' ATG and 3' GGC 3 bp sticky ends upon digestion with SapI (New England Biolabs, Beverly, Mass., USA). For the stuffers that do not have a C terminal extension (e.g. Ubiquitin, native and secreted) the address tags correspond precisely to the start (ATG) and stop (TAA) codons of the gene. For membrane or endosome anchored vectors, a GCC alanine linker is used instead of TAA stop, to facilitate the C terminal extensions needed for trafficking (i.e. GPI or endosomal targeting). Cleavage of the vector with SapI generates sticky ends compatible with the cleaved PCR product. The insert is thus directionally and precisely cloned into the vector. The majority of recovered colonies are recombinant, since the SapI generated sticky ends in the parental vector are not compatible. The vector and PCR product SapI sites are removed and are not incorporated into the final vector. Addition of SapI to the ligation reaction, to eliminate uncut or singly cut parental vector, selectively enriches for recombinant transformation colonies (this strategy can be used only for inserts without internal SapI sites). SapI sites within the target gene are generally not detrimental since there is only a 1/16 chance that an internal SapI site would match one of the address tags. An 8-96 well (PCR [96-well gradient block]) format can be used for high throughput applications (PCR, purification, digestion, ligation to SapI digested vector).

This example is not meant to limit cloning to SapI type IIS cloning. Alternative type IIS enzymes could also be utilized, such as AarI, which creates a 4 bp overlap for cloning.

Alternative cloning strategies could be utilized to clone into the series of vectors. For example, the PCR primers could incorporate modified bases that allow elimination of terminal bases of the primers to generate the overhangs needed for cloning. dU excision by uracil N-glycosylase (Smith C, Day P J, Walker M R. 1993 *PCR Methods Appl.* 2:328-32), ribonucleotide excision by rare earth metal ions (Chen G J, Qiu N, Page M P. 2002 *Biotechniques.* 32:516, 518-20) have been utilized to create cohesive ends. Alternatively, the RNA overhang cloning method using chimeric PCR primers with RNA sequences that cannot be copied by certain thermostable DNA polymerases to yield a 5' overhang identical to the sequence of the RNA component of the primer (Coljee V W, Murray H L, Donahue W F, Jarrell K A. 2000 *Nat. Biotechnol.* 18:789-91). This is not intended to be a comprehensive list. Various strategies to create short regions of overlap would be readily apparent to one of average skill in the art.

Vectors with traditional restriction enzyme sites could also be created and utilized. However, such vectors would contain additional sequences to specify the restriction sites, and therefore are less preferred since they increase the variability between backbones.

TypeIIS cloning is simpler than ligation independent cloning (LIC) for this application. With class IIS cloning a single primer pair facilitates cloning into three vectors, and two PCR products allow cloning into the entire family. This is because the overlap region of a single 3 bp codon can be duplicated seamlessly in the vector family. Ligation independent cloning requires longer regions of complementarity between vector and insert (minimum of 10 bp; Aslanidis C, de Jong P J, Schmitz G. 1994 *PCR Methods Appl.* 4:172-177); therefore, seamless cloning would require a unique combination of vector specific primers to clone a gene into each trafficking vectors. However, I contemplate LIC could be utilized to practice the invention, since LIC can also be seamless.

High throughput applications with these vectors could include functional genomic screens of genomes for protective antigens, by high throughput cloning of cDNA or genomic fragments into one or more vectors, and evaluation of vectors, or pools of vectors, for protective immunity or immune responses in vivo.

Example 11

Innate Immune Induction Utilizing Immunostimulatory RNA Producing DNA Vaccines

Immunostimulatory RNAs are well known in the art. While immunostimulatory responses may be species and cell type specific, matrix transfection of primary cell lines from the target tissues can be utilized to select the optimal combination of RNA elements for each vaccine/delivery combination.

Potential targets for immunostimulatory RNA elements are known in the art. Cytoplasmic dsRNA activates PKR and RIG-1 and MDA-5, which induces interferon production, inhibits protein synthesis thus reducing antigen production eventually leading to apoptotic cell death. RIG-1 and MDA-5 stimulation can induce TH1 bias through TNFα and IL12 production.

The utility of RNA elements to improve immunostimulatory activity of DNA vaccines was demonstrated as follows. The pDNAVACCultra5-EGFP-mU6 and pDNAVACCultra5-EGFP-SV40-mU6 (FIG. 2) derivatives of pDNAVACCultra5-EGFP and pDNAVACCultra5-EGFP-SV40, respectively, were constructed by ligating a 300 bp murine U6 Pol III promoter cassette into the blunt StuI site of the parent vector. The resultant constructs were sequence verified. This vector produces a 60 bp RNA, that includes the vector encoded trpA terminator hairpin. The linear vector NheI/HpaI digested) purified. RNA elements were cloned under U6 promoter control after annealing compatible oligonucleotides. (5' blunt-3' NheI compatible). The first base at the 5' end is a purine and is the first base of the transcribed RNA. A run of 4-6 thymidine residues to terminate PolIII transcription precedes the NheI site. A number of immunostimulatory ssRNA, shRNA and dsRNA elements described in the art were cloned into the vectors. Plasmid DNA (singly or in combinations) were transfected into murine Macrophage cell line RAW 267.4, muscle cell line C2C12 and fibroblast cell line PA317 at a concentration of 0.4 ug plasmid/mL using lipofectamine 2000 as described by the manufacturer (Invitrogen, Carlsbad, Calif., USA). The transfection media was removed after 4 hrs incubation, and EGFP expression determined by fluorescent microscopy at 24, 48 and 72 hrs.

High level EGFP expression was detected in all transfections, and was not reduced, compared to the parental vectors, by inclusion of the U6 driven RNA elements. This demonstrates compatibility of antigen expression cassettes and RNA elements within a single DNA vaccine plasmid. TNFα (an inflammatory cytokine indicative of $T_H1$ innate immune induction) levels in the culture supernatants from the RAW 267.4 transfected cells were determined at 36 hrs post transfection (Table 5) using a kit as described by the manufacturer (R&D Systems, Minneapolis, Minn.). Inclusion of an RNA element increased TNFα expression dramatically compared to the parent vector. Certain immunostimulatory RNA elements had, as predicted, greater induction of TNFα than the base vector which transcribes the vector encoded trpA terminator. Similar results were obtained in a repeat transfection of RAW 267.4, using 0.8 ug plasmid/mL Here, assaying at 15 hrs post transfection demonstrated dramatic induction of TNFα (Table 6). This demonstrates that inclusion of an immunostimulatory RNA element in a DNA vaccine vector backbone can increase vector mediated immunostimulation, without loss of antigen expression.

TABLE 5

Immunostimulatory RNA element induced TNFα production in RAW 264.7 cell line (36 hrs post transfection)

| Vector | RNA element | Form | TNFα (pg/mL) |
|---|---|---|---|
| pDNAVACCultra5-EGFP | No | | 61 |
| pDNAVACCultra5-EGFP-SV40 | No | | 226 |
| pDNAVACCultra5-EGFP-mU6 | Yes | Vector trpA terminator | 415 |

TABLE 5-continued

Immunostimulatory RNA element induced TNFα production in RAW 264.7 cell line (36 hrs post transfection)

| Vector | RNA element | Form | TNFα (pg/mL) |
|---|---|---|---|
| pDNAVACCultra5-EGFP-SV40-mU6 | Yes | Vector trpA terminator | 423 |
| pDNAVACCultra5-EGFP-SV40-mU6-dsRNA2 | Yes | dsRNA | 902 |
| pDNAVACCultra5-EGFP-SV40-mU6-ssRNA1-4 | Yes | ssRNA (4 plasmids) | 908 |
| pDNAVACCultra5-EGFP-SV40-mU6-shRNA1 | Yes | | 647 |
| pDNAVACCultra5-EGFP-SV40-mU6-shRNA2 | Yes | | 663 |
| pDNAVACCultra5-EGFP-SV40-mU6-shRNA3 | Yes | | 828 |
| pDNAVACCultra5-EGFP-SV40-mU6-shRNA4 | Yes | shRNA hairpin with microRNA loop | 810 |
| Lipofectamine control | No | | 62 |
| No transfection control | No | | 64 |

TABLE 6

Immunostimulatory RNA element induced TNFα production in RAW 264.7 cell line (15 hrs post transfection)

| Vector | RNA element | Form | TNFα (pg/mL) |
|---|---|---|---|
| pDNAVACCultra5-EGFP | No | | 475 |
| pDNAVACCultra5-EGFP-mU6 | Yes | Vector trpA terminator | 3175 |
| pDNAVACCultra5-EGFP-SV40-mU6-dsRNA2 | Yes | dsRNA | 4386 |
| pDNAVACCultra5-EGFP-SV40-mU6-ssRNA1-4 | Yes | ssRNA (4 plasmids) | 3662 |
| pDNAVACCultra5-EGFP-SV40-mU6-shRNA4 | Yes | shRNA hairpin with microRNA loop | 5338 |
| Lipofectamine control | No | | 29 |
| No transfection control | No | | 26 |

Example 12

Apoptosis Induction Utilizing shRNA Producing DNA Vaccines

Potential targets for apoptosis inducing shRNAs are shown in FIG. 10. Arc and Flip are expressed at high levels in skeletal muscles, while Flip is expressed at high levels in keratinocytes. Targeted reduction of single genes, or combinations of these gene products by RNA elements can be used to sensitize cells that have uptaken the DNA vaccine plasmid to cell death signals, to increase cell death. While this may be species and cell type specific, matrix transfection of primary cell lines from the target tissues can be utilized to select the optimal combination of RNA elements for each vaccine/delivery combination.

Example 13

Plasmid Expression Induction Using shRNA Producing DNA Vaccines

Ubiquitous NFκB Inhibitor proteins ($\alpha,\beta$, or $\epsilon$ subunits) are short halflife repressors of NFκB nuclear localization. RNA elements producing inhibitor shRNAs to one or more of these targets will cause NFκB activation and nuclear localization, which will both increase nuclear localization and expression from NFκB site containing expression plasmids (such as SV40 containing pDNAVACCUltra plasmids). While the optimal target subunits may be species and cell type specific, matrix transfection of primary cell lines from the target tissues can be utilized to select the optimal combination of RNA elements for each vaccine/delivery combination.

Example 14

RapidVACC Vaccine Development Algorithm

An overview of the RapidVACC algorithm for creation and evaluation of an antigen specific DNA vaccine is shown (FIG. 8). A prescreen in primary cells from the relevant tissue in the target organism can be utilized to screen and select optimal RNA elements for inclusion in the first round. The first round is where RNA element containing plasmids are assessed for apoptosis, innate immune stimulation and ultimately improved immune response. Although shown here as a single round of optimization, initially two or more cycles may be performed to further optimize the RNA expression cassettes by combination of promising elements from the initial screen. Once the vector backbone is locked (Milestone 1) each additional cycle of animal study optimization (e.g. presentation optimization, mixed presentation optimization) may additively or synergistically improve vaccine performance, and the final vaccine performance does not rely solely on success within a single parameter. The development time for this would be dramatically shorter (2-3 weeks to make and produce vaccine), since backbone and presentation are determined. Once the platform is developed, a standard development timeline for new antigens (with existing rapid animal model), without expediting, is shown (FIG. 8).

The optimal presentation is anticipated to be antigen and delivery specific. Electroporation targets muscle cells and likely delivers antigens for immune presentation via cross presentation to APC. This may optimally require secreted and/or stable protein in the donor cell, along with cell death to attract and stimulate APC's. For Gene Gun, which targets dendritic cells, direct priming may be the dominant antigen presentation mode and proteosomal and/or endosomal targeted antigen, for enhanced MHCI or MHCII presentation, respectively, may be optimal. Combinations of plasmids, optimized for each modality, may ultimately provide superior protection. For example combinations of vectors expressing native, dendritic- and proteosomal-targeted SIV antigens provided superior protection in rhesus macaques (Rosati et al, Supra, 2005); similar enhancement was observed with mixed plasmids encoding cytoplasmic and ubiquitin conjugated papillomavirus capsid genes (Liu et al. Supra, 2001).

Ultimately, combinations of dsRNA, ssRNA and/or apoptosis inducing shRNAs may provide superior innate immune response compared to the initial single component vectors evaluated here. Due to the small size of the pol III transcription units, multiple components can eventually be incorporated into the final vaccine. As well, with combination vaccines where more than one plasmid is contemplated (as with Influenza, wherein more than one antigen expressing plasmids may be combined), different components can be present on each plasmid.

Conclusions, Ramifications and Scope of the Invention

Thus, the reader will see that the genetic vaccine vectors of the invention provide for a rationale approach to optimization of genetic immunization, through use of vector encoded targeting molecules.

While the above description contains many specificities, these should not be construed as limitations on the scope of the invention, but rather as an exemplification of one preferred embodiment thereof. Many other variations are possible. For example, MDA5, RIG-1 and PKR activating immunostimulatory RNA elements may be combined with repressor RNA elements that encode shRNAs to inhibit LGP2 (a repressor of RIG-1 and MDA5 sdRNA immunostimulation) and/or inhibitors of PKR. This would maximize immunostimulation while preventing PKR mediated inhibition of antigen expression. Other inhibitor RNA elements could be included to induce apoptosis selectively in non-immune cells, to increase antigen cross presentation, or influence $T_H1$ versus $T_H2$ bias.

Accordingly, the scope of the invention should be determined not by the embodiments illustrated, but by the appended claims and their legal equivalents.

I claim:

1. A method for modifying the response of an individual to a pDNAVACCUltra-derived plasmid expression vector comprising the steps of:
   a. cloning one or more genes that encode a protein or peptide antigen into a pDNAVACCUltra-derived plasmid expression vector that contains one or more immunostimulatory RNA elements that do not collectively activate protein kinase R, the pDNAVACCUltra-derived plasmid expression vector having the immunostimulatory RNA elements inserted between a convergently oriented eukaryotic transcriptional terminator and a pMB 1 or pUC origin; and
   b. delivering the expression vector to a eukaryotic cell; and
   c. evaluating immune response or protection after vector delivery.

2. The method of claim 1, wherein said RNA element(s) are selected from the group consisting of: TLR-3 activating RNA; TLR-7 activating RNA; TLR-8 activating RNA; RIG-I activating RNA; Mda-5 activating RNA; RIG-I and Mda5 activating RNA; TLR-3 and PKR activating RNA combined with PKR inhibiting RNA; TLR-7 and PKR activating RNA combined with PKR inhibiting RNA; TLR-8 and PKR activating RNA combined with PKR inhibiting RNA; RIG-I and PKR activating RNA combined with PKR inhibiting RNA; Mda5 and PKR activating RNA combined with PKR inhibiting RNA; RIG-I, Mda5, and PKR activating RNA combined with PKR inhibiting RNA; TLR-3, TLR-7, TLR-8, RIG-I, Mda5, and PKR activating RNA combined with PKR inhibiting RNA; and combinations thereof.

3. The method of claim 1, wherein said RNA element(s) are used to promote one or more innate immune responses.

4. The method of claim 1, wherein said RNA element(s) are used to promote one or more adaptive immune responses.

5. The method of claim 1, wherein said RNA element(s) are additionally combined with one or more RNA(s) to alter more than one cellular function or pathway.

6. The method of claim 1, wherein said RNA element(s) are selected from the group consisting of those that produce: a single stranded RNA; a double stranded RNA; a hairpin RNA; a microRNA; a RNA aptamer; a ribozyme, and combinations thereof.

7. The method of claim 1, wherein said individual is a mammal, bird or fish.

8. A method for modifying the response of an individual to a pDNAVACCUltra-derived plasmid expression vector comprising the steps of:
   a. cloning one or more genes that encode a protein or peptide into a pDNAVACCUltra-derived plasmid expression vector that contains one or more immunostimulatory RNA elements that do not collectively activate protein kinase R, the pDNAVACCUltra-derived plasmid expression vector having the immunostimulatory RNA elements inserted between a convergently oriented eukaryotic transcriptional terminator and a pMB1 or pUC origin, the pDNAVACCUltra-derived plasmid expression vector including a prokaryotic region having a replication origin and a Kanamycin resistance gene; and
   b. delivering the expression vector to a eukaryotic cell; and
   c. evaluating immune response or protection after vector delivery.

* * * * *